(12) United States Patent
Nelsen et al.

(10) Patent No.: US 11,903,572 B2
(45) Date of Patent: Feb. 20, 2024

(54) SURGICAL INSTRUMENTS, SYSTEMS, AND METHODS WITH OPTICAL SENSORS

(71) Applicant: NuVasive, Inc., San Diego, CA (US)

(72) Inventors: Christopher Nelsen, San Diego, CA (US); Michael Serra, San Diego, CA (US)

(73) Assignee: NuVasive, Inc., San Diego, CA (US)

( * ) Notice: Subject to any disclaimer, the term of this patent is extended or adjusted under 35 U.S.C. 154(b) by 198 days.

(21) Appl. No.: 17/474,537

(22) Filed: Sep. 14, 2021

(65) Prior Publication Data

US 2023/0085418 A1 Mar. 16, 2023

(51) Int. Cl.
*A61B 17/02* (2006.01)
*A61B 90/00* (2016.01)
*A61B 17/16* (2006.01)
*A61B 17/3211* (2006.01)

(52) U.S. Cl.
CPC ...... *A61B 17/0206* (2013.01); *A61B 17/1615* (2013.01); *A61B 90/04* (2016.02); *A61B 90/06* (2016.02); *A61B 2017/32113* (2013.01); *A61B 2090/064* (2016.02); *A61B 2562/0238* (2013.01); *A61B 2562/223* (2013.01)

(58) Field of Classification Search
CPC ..... A61B 90/04; A61B 90/06; A61B 17/1615; A61B 2090/064; A61B 2017/32113; A61B 2562/0238; A61B 2562/223
See application file for complete search history.

(56) References Cited

U.S. PATENT DOCUMENTS

| | | |
|---|---|---|
| 3,807,390 A | 4/1974 | Ostrowski |
| 4,443,698 A | 4/1984 | Schiffner |
| 4,784,150 A | 11/1988 | Voorhies et al. |
| 5,010,772 A | 4/1991 | Bourland |
| 5,769,781 A | 6/1998 | Chappuis |
| 5,828,059 A | 10/1998 | Udd |
| 5,833,608 A | 11/1998 | Acker |
| 5,876,325 A | 3/1999 | Mizuno |

(Continued)

FOREIGN PATENT DOCUMENTS

| | | |
|---|---|---|
| WO | 2001033165 A1 | 5/2001 |
| WO | 2020079598 A1 | 4/2020 |
| WO | 2021127738 A1 | 7/2021 |

OTHER PUBLICATIONS

Micronor Inc., Micronor Fiber Optic Kinetic Sensors Company and Product Overview (Apr. 30, 2019).

(Continued)

*Primary Examiner* — Zade Coley
*Assistant Examiner* — Diana Jones
(74) *Attorney, Agent, or Firm* — Seager, Tufte & Wickhem, LLP

(57) ABSTRACT

Medical or surgical devices, instruments, systems, and methods for use in optically sensing loads acting on a patient's anatomy may include a surgical device or instrument configured for insertion to a surgical site and an interrogator coupled to the surgical device or instrument via an optical fiber having a sensing area at a location of the surgical device or instrument at which a load is to be sensed. The measured load may be used as being indicative of a load acting on a patient's anatomy. Such measured or determined load may be used to make decisions before, during, or after a patient procedure.

13 Claims, 14 Drawing Sheets

(56) References Cited

U.S. PATENT DOCUMENTS

| | | | |
|---|---|---|---|
| 5,989,700 | A | 11/1999 | Krivopal |
| 6,004,341 | A | 12/1999 | Zhu et al. |
| 6,272,936 | B1 | 8/2001 | Oreper |
| 6,829,507 | B1 | 12/2004 | Lidman et al. |
| 6,888,623 | B2 | 5/2005 | Clements |
| 6,905,460 | B2 | 6/2005 | Wang |
| 7,196,320 | B1 | 3/2007 | Rickenbach |
| 7,445,598 | B2 | 11/2008 | Orban, III |
| 8,461,514 | B1 | 6/2013 | Rickenbach |
| 8,827,900 | B1 | 9/2014 | Pimenta |
| 8,989,528 | B2 | 3/2015 | Udd |
| 9,636,096 | B1 * | 5/2017 | Heaton ............ A61B 5/14542 |
| 9,687,357 | B2 | 6/2017 | Bannigan et al. |
| 9,918,642 | B2 | 3/2018 | Hecker et al. |
| 10,350,084 | B1 | 7/2019 | Lin et al. |
| 10,973,650 | B2 | 4/2021 | Stein |
| 2003/0135204 | A1 | 7/2003 | Lee |
| 2004/0165810 | A1 | 8/2004 | Fujita |
| 2005/0137478 | A1 | 6/2005 | Younge |
| 2005/0215866 | A1 | 9/2005 | Kim |
| 2007/0151391 | A1 * | 7/2007 | Larkin ................ A61B 34/76 74/490.06 |
| 2008/0285909 | A1 | 11/2008 | Younge |
| 2008/0319268 | A1 | 12/2008 | Michaeli et al. |
| 2011/0319714 | A1 | 12/2011 | Roelle |
| 2011/0319815 | A1 | 12/2011 | Roelle |
| 2013/0190734 | A1 | 7/2013 | Taylor et al. |
| 2013/0317303 | A1 | 11/2013 | Deshmukh |
| 2015/0088030 | A1 | 3/2015 | Taylor |
| 2015/0164598 | A1 * | 6/2015 | Blumenkranz ...... B25J 15/0009 606/130 |
| 2017/0196479 | A1 * | 7/2017 | Liu ..................... G01K 13/20 |
| 2017/0258315 | A1 | 9/2017 | Gharib et al. |
| 2017/0312039 | A1 | 11/2017 | Crawford |
| 2019/0262140 | A1 | 8/2019 | Bannigan |
| 2020/0018647 | A1 | 1/2020 | Waltermann |
| 2020/0069377 | A1 | 3/2020 | Finley |
| 2021/0145365 | A1 * | 5/2021 | Howard ................ A61B 18/02 |

OTHER PUBLICATIONS

International Search Report and Written Opinion dated Jan. 2, 2023 for International Application No. PCT/US2022/043406.

* cited by examiner

SURGICAL INSTRUMENTS, SYSTEMS, AND METHODS WITH OPTICAL SENSORS

BACKGROUND

A wide variety of surgical and medical devices, instruments, and systems have been developed for surgical and medical uses. Some of these devices, instruments, and systems include instruments used in spinal surgeries and the like. These devices, instruments, and systems are manufactured by any one of a variety of different manufacturing methods and may be used according to any one of a variety of methods. Of the known medical devices, instruments, systems, and methods, each has certain advantages and disadvantages.

BRIEF SUMMARY

This disclosure provides design, material, manufacturing method, and use alternatives for surgical and medical devices, instruments, and systems. There is an ongoing need to provide alternative surgical and medical devices, instruments, and systems, as well as alternative methods for manufacturing and using surgical and medical devices, instruments, and systems.

An example surgical system may include a surgical device having an optical fiber and configured for insertion to a surgical site, an interrogator coupled to the optical fiber, wherein the interrogator is configured to sense light reflected through the optical fiber and translate the sensed light into electrical signals. The surgical device includes a tissue contacting component having a first portion, wherein the first portion is responsive to loads acting on the tissue contacting component, and the optical fiber disposed along the first portion of the tissue contacting component, wherein the optical fiber is configured to deform in response to loads acting on the tissue contacting component. The electrical signals may be indicative of the loads acting on the tissue contacting component of the surgical device.

Alternatively or additionally to any of the embodiments in this section, the optical fiber is configured to be removed from the surgical device.

Alternatively or additionally to any of the embodiments in this section, the surgical device comprises a body defining at least part of the first portion of the tissue contacting component, the body having an electrode configured for use in sensing nerve tissue adjacent the surgical device, and the optical fiber.

Alternatively or additionally to any of the embodiments in this section, at least a portion of the optical fiber is permanently fixed along the tissue contacting component.

Alternatively or additionally to any of the embodiments in this section, the surgical device comprises a removable body configured to be used in sensing nerve tissue adjacent the surgical device, wherein an electrode is disposed in the removable body and the removable body is slidably coupled to the surgical device.

Alternatively or additionally to any of the embodiments in this section, the first portion of the tissue contacting component is constructed from a first material and a second portion of the tissue contacting component is constructed from a second material.

Alternatively or additionally to any of the embodiments in this section, the first material is more responsive to loads acting on the tissue contacting component than the second material.

Alternatively or additionally to any of the embodiments in this section, the optical fiber includes a sensing portion disposed along the first material.

Alternatively or additionally to any of the embodiments in this section, the optical fiber includes a sensing portion disposed along the first portion of the tissue contacting component.

Alternatively or additionally to any of the embodiments in this section, the interrogator includes a light emitter configured to emit a light through the optical fiber.

Alternatively or additionally to any of the embodiments in this section, the interrogator includes a detector configured to sense the light reflected through the optical fiber and the light reflected through the optical fiber is emitted from the light emitter.

Alternatively or additionally to any of the embodiments in this section, the surgical device is a device selected from a group consisting of a surgical implant, a surgical retractor, a surgical dilator, a trial implant, a surgical drill bit, and a surgical measurement tool.

In a further example, a pressure sensing surgical device may include a component configured to be adjusted at or near a surgical site, the component has a tissue contacting surface, an optical fiber extending adjacent to or through the component, and a sensing portion of the optical fiber, the sensing portion of the optical fiber being configured to deform in response to loads acting on the tissue contacting surface caused by adjustment of the component.

Alternatively or additionally to any of the embodiments in this section, the sensing portion of the optical fiber has a length within a range of three inches to nine inches.

Alternatively or additionally to any of the embodiments in this section, the sensing portion of the optical fiber includes up to twenty-five fiber Bragg gratings, wherein the fiber Bragg gratings have a grating period of at least 1 millimeter (mm), and wherein the fiber Bragg gratings include at least two fiber Bragg gratings having a grating period of 1 mm and at least two fiber Bragg gratings having a grating period of 10 mm.

Alternatively or additionally to any of the embodiments in this section, the component is a retraction blade coupled to a retraction body.

Alternatively or additionally to any of the embodiments in this section, the component is an expandable implant.

Alternatively or additionally to any of the embodiments in this section, the component is an expandable trial implant.

Alternatively or additionally to any of the embodiments in this section, the component includes a portion constructed from a first material and a portion constructed from a second material, the sensing portion of the optical fiber is disposed along the second material.

Alternatively or additionally to any of the embodiments in this section, the second material is less rigid than the first material.

Alternatively or additionally to any of the embodiments in this section, the device may include a plurality of optical fibers extending adjacent the component, the plurality of optical fibers including the optical fiber.

Alternatively or additionally to any of the embodiments in this section, the component is a surgical drill bit.

In a further example, a method may include positioning a surgical device proximate a surgical site, detecting, with an interrogator, light reflected through an optical fiber extending along the surgical device, and determining a load that is applied to tissue at or adjacent the surgical site by the surgical device based on the light reflected through the optical fiber that is detected.

Alternatively or additionally to any of the embodiments in this section, the surgical device is a retractor, positioning the surgical device includes using the retractor to form a surgical corridor to the surgical site, and the method includes applying an electrical stimulation, with an electrode of the retractor, to tissue at or adjacent the surgical site to detect a presence of nerve tissue.

Alternatively or additionally to any of the embodiments in this section, when the presence of the nerve tissue has been detected, determining the load that is applied to the tissue at or adjacent the surgical site includes estimating a load applied to the nerve tissue.

Alternatively or additionally to any of the embodiments in this section, the method further includes in response to detecting the presence of the nerve tissue, displaying on a user interface an indication that the nerve tissue has been detected and a load applied to the nerve tissue.

Alternatively or additionally to any of the embodiments in this section, the method further includes customizing a threshold based on a proximity of the nerve tissue detected based on the electrical stimulation, comparing the load applied to the nerve tissue by the surgical device to the threshold, and in response to determining the load applied to the nerve tissue passes the threshold, initiating a timer.

Alternatively or additionally to any of the embodiments in this section, the method further includes in response to detecting the presence of the nerve tissue, displaying on a user interface an indication that the nerve tissue has been detected, a load applied to the nerve tissue, and a length of time the load applied to the nerve tissue has been above the threshold.

Alternatively or additionally to any of the embodiments in this section, the method further includes when at the surgical site, adjusting a position of a component of the surgical device, and determining a position of the component based on the light reflected through the optical fiber that is detected.

Alternatively or additionally to any of the embodiments in this section, the surgical device is a surgical device selected from a group consisting of a surgical implant, a surgical retractor, a surgical dilator, a trial implant, a surgical drill bit, and a surgical measurement tool.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
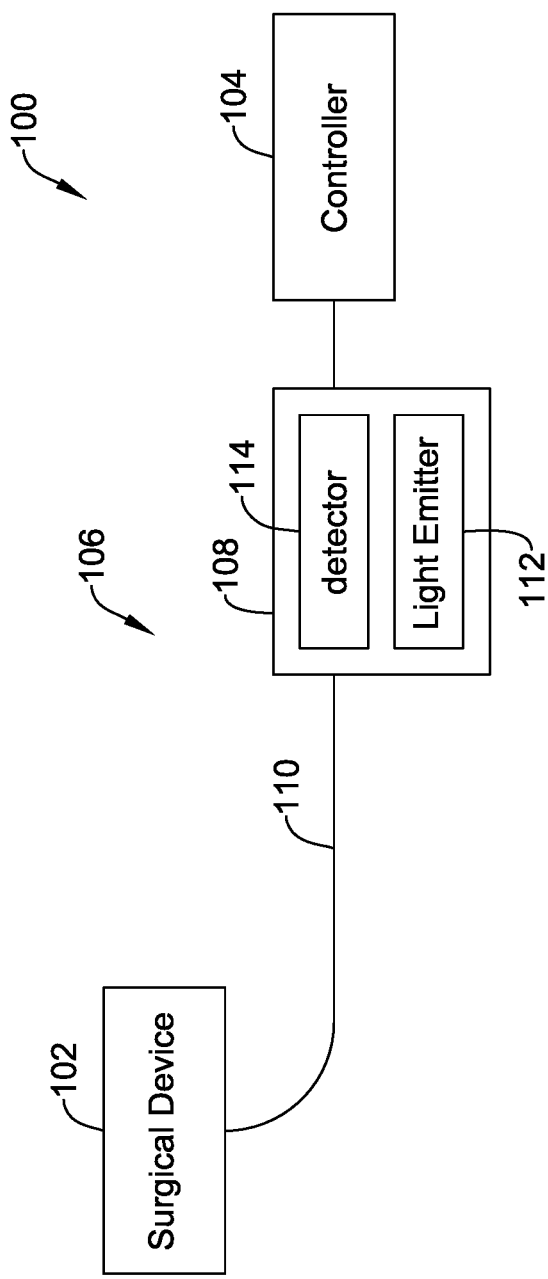
FIG. 1 is a schematic diagram of an illustrative system for sensing loads applied to a surgical device.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

Surgical and medical devices and instruments (e.g., tools, implants, etc.) are used in various procedures in which the devices and instruments have loads (e.g., strain, pressure, vibration, temperature, or force) applied thereto (e.g., in response to operating the devices or instruments, in response to applying loads to a patient's anatomy, or in response to other uses of the devices or instruments). In one example, during a minimally invasive surgical procedure on a patient, a need may arise to increase a size of a surgical site (e.g., increase an intervertebral disc space to accommodate an implant or decompress a nerve). In another example, blades of a retractor may apply a force to retract the patient's anatomy. It can be advantageous for a user to understand the forces applied to the blades and thus, the patient's anatomy, as well as the strain distribution throughout the instrument, when the blades interact with the patient's anatomy. Similarly, it may be advantageous for a user to understand the loads applied to a patient's anatomy by other devices and instruments used in medical and surgical procedures. In some cases, knowing the loads may facilitate determining a positioning or location of the devices and instruments used within the patient's anatomy.

Attempts have been made to place force sensors in surgical devices and instruments, however, such uses of force sensors have been difficult to implement. In one example, it has been attempted to place thin film force sensors in surgical and medical devices and instruments, but it has proven impractical to embed such sensors in a manner that allows for desired use of the devices and instruments and provides meaningful force, strain data, or both force and strain data to users of the medical and surgical devices and instruments.

Using optical sensing systems with medical and surgical devices and instruments may provide users with data in a manner that can have a meaningful impact on how the medical and surgical devices and instruments are used. In some cases, the data may be used in real time to make decisions during a surgical procedure. Additionally or alternatively, the data may be used and analyzed post-procedure to determine or assess an effectiveness of the procedure. The data may be utilized in one or more other suitable manners in a procedure room or at a remote location.

Strain, pressure, vibration, temperature, force, and positioning may be sensed using one or more fiber optic cables embedded in medical and surgical instruments and devices (e.g., surgical tools, implants, etc.), where the fiber optic cables have fiber Bragg gratings (FBGs) therein. In one example, an optical sensing system may include FBGs on a fiber optic cable (e.g., a fiber optic sensor chain) and an interrogator may be in or utilized with a surgical device or instrument to provide stress and strain information before, during, or after spinal surgeries.

The fiber optic cable may connect to an interrogator that acts as a spectrometer, signal processor, or both. The interrogator may broadcast light through the fiber and "grates" along the length of the fiber may reflect light back to the interrogator. As the fiber optic cable changes shape (e.g., deforms) in response to loads acting thereon, the grates may change shape or positioning and reflect back to the interrogator changes (e.g., deltas) in light wavelengths that may be detected and used to determine loads acting on the fiber optic cable.

In one example fiber optic cable configuration, a portion of a fiber optic cable embedded in a surgical instrument may have up to 25 unique FBGs, or more, at a minimum spacing of one millimeter (mm) or other suitable spacing. In some cases, an outer diameter of the embedded fiber optic cables may be within a range from about 0.15 mm (e.g., bare) to about 1.6 mm (e.g., with PEEK tubing), but other suitable outer diameters are contemplated.

In some cases, the optical sensing systems may be implemented in or with a surgical instrument or other suitable surgical or medical device or instrument. For example, the fiber optic sensing systems discussed herein may be utilized with or in retractors, electrodes, drill bits, drills, bone saws, implants, trial implants (i.e., implant sizing or testing components), expanders, or other suitable surgical or medical instruments and devices. When an optical sensing system is implemented in a surgical instrument, light may be reflected back to the interrogator and digitized into usable data and presented to a user (e.g., a surgeon, technician, or other suitable medical provider) via a user interface while a load is applied to the fiber optic cable during surgical actions (e.g., the fiber optic cable becomes loaded through the surgical instrument). This may allow the user to identify real time changes in stress and strain on the surgical instrument and stress and strain on or proximate patient anatomy as the device or instrument is used in the surgical procedure and the data may be used to affect how the user positions or otherwise interacts with the instrument. Further, the usable data may be utilized for assessing the procedure at a later time (e.g., post procedure or other suitable time).

Turning to the Figures, FIG. 1 depicts a schematic diagram of an illustrative system 100 for determining mechanical properties or other suitable properties or conditions acting on a surgical instrument or device 102, which may be indicative of loads acting on an anatomy of a patient (e.g., a subject) by the surgical instrument or device 102. Although the system 100 is described with respect to and including the surgical instrument or device 102, the system 100 may be similarly implemented with respect to a medical device or instrument.

In FIG. 1, the system 100 may include a controller 104, an optical fiber-based sensor system 106 (e.g., a load sensing system, such as a pressure, force, strain, temperature, or other suitable load sensing system), and the surgical device 102 (e.g., which may be a pressure, force, strain, temperature, or other load sensing surgical device when included with or coupled to the optical fiber-based sensor system 106 or at least a fiber optic cable 110 thereof). The optical fiber-based sensor system 106 may be in communication with the controller 104 and may include a housing separate from a housing of the controller 104 or the controller 104 and the optical fiber-based sensor system 106 may share a housing. Although the optical fiber-based sensor system 106 is primarily described herein as detecting or sensing measures of force or strain, the optical fiber-based sensor system 106 may detect or sense other loads, as discussed herein or otherwise.

The optical fiber-based sensor system 106 may include an interrogator 108 and the fiber optic cable 110 (e.g., a portion of which may be included in the surgical instrument or device 102), among other suitable components, where the fiber optic cable 110 may extend from the interrogator 108 to the surgical device 102. The interrogator 108 may be configured to provide light to the fiber optic cable 110 and collect light reflected back through the fiber optic cable 110 indicative of a force (e.g., a pressure) or strain, or other mechanical property, acting on the fiber optic cable 110. The interrogator 108 may include a light emitter 112 (e.g., a light source) for providing light to the fiber optic cable 110 and a detector 114 (e.g., a light detector) for detecting or collecting light reflected back through the fiber optic cable 110.

Figure 2:
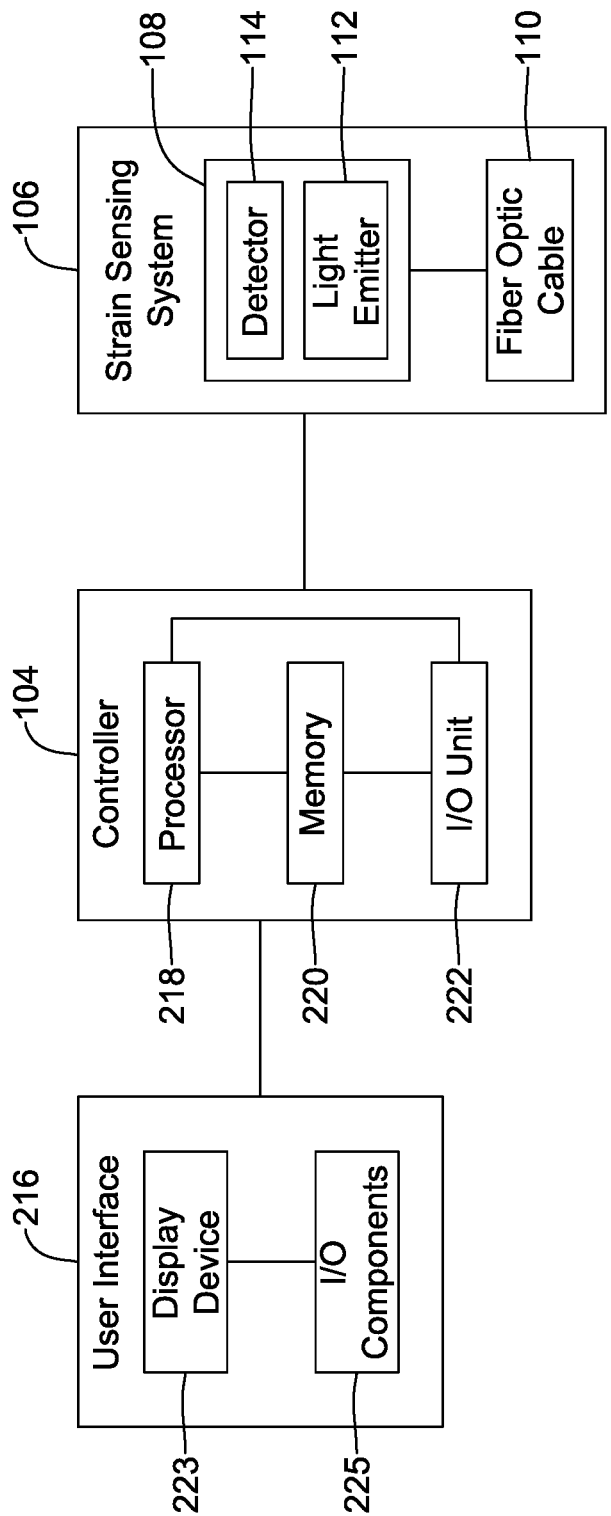
FIG. 2 is a schematic diagram of an illustrative system for sensing loads.

FIG. 2 depicts a schematic diagram of the optical fiber-based sensor system 106 in communication with the controller 104 and a user interface 216. The combination of the controller 104, the optical fiber-based sensor system 106, and the user interface 216 may be used for determining or establishing mechanical properties or other suitable properties or conditions acting on a medical or surgical device or instrument 102, which may be related to forces acting on a patient's anatomy that is in contact with the device or instrument 102. The controller 104, the optical fiber-based sensor system 106, and the user interface 216 may be located in a single housing component or two or more separate housings, as desired, which may be adjacent one another or remote from one another.

The optical fiber-based sensor system 106 may be any suitable type of optical fiber-based sensor system configured to sense force or strain along a medical or surgical device or instrument 102. In one example, the optical fiber-based sensor system 106 may be a fiber optic distributed strain sensing (DSS) system, which may use multiple data points corresponding to locations along a length of the fiber optic cable 110 to identify a force or strain distribution along the medical or surgical device or instrument 102.

The controller 104 may be any suitable controller configured to process the data of or from the optical fiber-based sensor system 106. The controller 104 may be a component that is separate from the optical fiber-based sensor system 106, as depicted in FIG. 2, or the controller 104, or a portion of the controller 104, may be a component of or otherwise included in the optical fiber-based sensor system 106.

As discussed above, the optical fiber-based sensor system 106 may include, among other suitable components, the fiber optic cable 110 and the interrogator 108 that include the detector 114 and the light emitter 112, both of which may be in communication with the fiber optic cable 110. The detector 114 (e.g., a light detector and/or other suitable type of detector) may be connected to a first end of the fiber optic cable 110 and may be configured to detect light that is reflected back to the first end after interacting with a material (e.g., glass or other suitable material) of a fiber of the fiber optic cable 110.

The fiber optic cable 110 may include one or more optical fibers configured to allow light to travel along each fiber. In one example, the fiber optic cable 110 may be a sensor chain. Although not required, the sensor chain may include a plurality of optical fibers.

The fiber optic cable 110 and the fibers thereof may take on any suitable configuration. For example, the fiber optic cable 110 may include a distal portion at which the one or more fibers are bare or covered by a first material and a proximal portion at which the one or more fibers are covered with a second material. The first and second materials may be any suitable materials or combinations of materials. In one example, the first material may be a silica capillary material, a PEEK tubing material, a stainless steel capillary material, or other suitable material. In another example, the second material may be a glass textile material, a corrugated stainless steel tubing, or other suitable material.

The fiber optic cable 110 and fibers thereof may have any suitable size and configuration. In one example, an outer diameter of a fiber of the fiber optic cable 110 may be in a range of about 0.15 millimeters (mm) to about 1 mm, or other suitable range. In another example, an outer diameter of the fiber optic cable 110 may be in a range of about 1.6 mm to about 3 mm, or other suitable range.

In some cases, the fiber optic cable 110 and the one or more fibers thereof may include a sensing area (e.g., a sensing portion) that includes FBGs facilitating distributed sensing of forces along a surgical or medical device or instrument in addition to at one or more desired locations. An optical fiber-based sensor system 106 incorporating such a fiber optic cable 110 may have the advantages of being relatively rugged and miniature when compared to other force and strain sensors (e.g., thin-film sensors or other sensors). Additionally, fiber optic sensing with FBGs may be immune to radio frequency (RF) and electromagnetic fields and high voltage, which may be beneficial for use in surgical procedure rooms that include imaging systems and other systems that may emit RF or electromagnetic fields.

An FBG is a microstructure formed within a core of an optical fiber comprising a periodic modulation of a refractive index of an underlying glass material of the fiber. When light (e.g., broadband light) hits the microstructure having the periodic modulation, one specific wavelength band is reflected, and all other wavelengths are transmitted through the fiber. That is, the microstructure that is inscribed into the glass for each FBG may define a specific wavelength band that is reflected. Thus, if local conditions (e.g., temperature, strain, etc.) change at an FBG, the period modulation of the FBG will change slightly in a known manner causing the wavelength band that the FBG reflects to shift. Typically, when a fiber at an FBG is compressed, the reflected wavelength decreases relative to when no strain is applied at the FBG and when a fiber at the FBG is stretched, the reflected wavelength increases relative to when no strain is applied at the FBG. These effects may be exploited to form an FBG sensor.

Temperature and/or strain may each affect the refractive index and/or grating period of the FBG, resulting in a reflection wavelength shift. While an FBG may generally respond (in wavelength shift) to both temperature and strain, an FBG may be packaged (e.g., housed) in order to modulate or control the physical conditions observed at the FBG. For example, an FBG may be packaged in order to decouple the FBG from temperature. When so packaged, changes in reflection wavelength for an FBG may be attributed primarily to a change in refractive index of the fiber caused by bending, tension, compression, torsion, or other forces on the FBG.

In one example fiber optic cable 110, the fiber optic cable 110 may include a single fiber spliceless chain with multiple FBGs formed into the fiber. Such a configuration may allow for a multipoint, distributed sensing solution for force or strain measurements. Other configurations are contemplated.

The light emitter 112 may be any suitable type of light emitter 112 configured to provide light through one or more fibers of the fiber optic cable 110. In some cases, the light emitter 112 may incorporate one or more lasers, one or more light emitting diodes (LEDs), one or more super luminescent light emitting diodes (SLEDs), or other suitable light sources configured to send light waves through the one or more fibers of the fiber optic cable 110. In one example, the light emitter 112 may be a fento second laser (fs-Laser).

The light emitter 112 may emit a light having a known wavelength. In some cases, the light emitter 112 may emit light at a wavelength within a range of 405 nanometers (nm) to 1580 nm, 800 nm to 880 nm, 800-865 nm, or light at one or more other suitable wavelengths.

The detector 114 may be any suitable type of light detector. In some cases, the detector 114 may be configured to detect light that has been reflected to the detector 114 through the fiber optic cable 110, as discussed herein. In one example, the detector 114 may be configured to detect an amount of light received at the detector 114, a pattern of light received at the detector 114, a wavelength of light received at the detector 114, one or more other suitable parameters related to light received at the detector 114, or combinations thereof. Although not required, measurements of the amount, the pattern, the wavelength, or other suitable parameters related to light received at the detector 114 may be saved in memory of the optical fiber-based sensor system 106 or other suitable memory.

A number of different light emitter 112 and detector 114 combinations may be employed in the interrogator 108. In one illustrative configuration, a broadband continuous light source may be used in conjunction with a dispersive element that distributes various wavelength components of the reflected light to different locations on a detector array. In another illustrative configuration, a tunable laser may be swept over a range of wavelengths, and a photodetector may measure the intensities of reflected light corresponding to the wavelengths provided by the laser at given sweep times. Other light emitter 112 and detector 114 combinations are contemplated, and any suitable combination of light emitter 112 and detector 114 may be employed in the interrogator 108.

In addition to or alternatively to the fiber optic cable 110 and the interrogator 108 including the detector 114 and the light emitter 112, the optical fiber-based sensor system 106 may include one or more other suitable components to facilitate sensing strain along the fiber optic cable 110. In one example, the optical fiber-based sensor system 106 may include, among other features, one or more processors, memory, input/output (I/O) units, communication components, user interfaces, touch screens, display screens, selectable buttons, housings, and/or other suitable components configured to facilitate sensing strain along the fiber optic cable 110. In some cases, the detector 114 or the light emitter 112 may be or may include computing devices having memory, one or more processors, and/or other suitable components of computing devices.

As depicted in FIG. 2, the controller 104 may be in communication with the optical fiber-based sensor system 106. In some cases, the controller 104 may be configured to receive data from the optical fiber-based sensor system 106 and may determine an amount of force or strain acting on a medical or surgical device incorporating the optical fiber-based sensor system 106.

Example data the controller 104 may receive from the optical fiber-based sensor system 106 may include, but is not limited to, values related to strain sensed by the optical fiber-based sensor system 106, time data associated with the optical fiber-based sensor system 106, or other suitable data. Additionally to or alternatively to receiving data from the optical fiber-based sensor system 106, the controller 104 may compare received data to one or more thresholds, compare received data to previously received data, determine an amount of time a change of force or strain has been detected at the surgical or medical device or instrument, determine an elapsed time since a detected force has passed a threshold, compare received data and an outcome for a procedure to data and outcomes of other procedures, or perform one or more other suitable data analyses. Additionally or alternatively, the controller 104 may be configured to sound an alarm, provide an alert, may determine when nerve tissue is detected, or take one or more other suitable actions based on the received data.

The illustrative controller 104 may include, among other suitable components, one or more processors 218, memory 220, and/or an I/O unit 222. Example other suitable components of the controller 104 that are not expressly depicted in FIG. 2 as being part of the controller 104 may include, but are not limited to, communication components, a user interface, a touch screen, a display screen, selectable buttons, a housing, a nerve sensing controller for use with an electrode, a device or instrument controller, or other suitable components of a controller. As discussed above, one or more components of the controller 104 may be separate from the optical fiber-based sensor system 106, as depicted in FIG. 2, or may be incorporated into the optical fiber-based sensor system 106.

The processor 218 of the controller 104 may include a single processor or more than one processor working individually or with one another. The processor 218 may be configured to execute instructions, including instructions that may be loaded into the memory 220 and/or other suitable memory. Example components of the processor 218 may include, but are not limited to, central processing units, microprocessors, microcontrollers, multi-core processors, graphical processing units, digital signal processors, application specific integrated circuits (ASICs), artificial intelligence accelerators, field programmable gate arrays (FPGAs), discrete circuitry, and/or other suitable types of data processing devices.

The memory 220 of the controller 104 may include a single memory component or more than one memory component each working individually or with one another. Example types of memory 220 may include random access memory (RAM), EEPROM, FLASH, suitable volatile storage devices, suitable non-volatile storage devices, persistent memory (e.g., read only memory (ROM), hard drive, flash memory, optical disc memory, and/or other suitable persistent memory) and/or other suitable types of memory. The memory 220 may be or may include a non-transitory computer readable medium. The memory 44 may include instructions stored in transitory and/or non-transitory state on a computer readable medium that may be executable by the processor 42 to cause the processor to perform one or more of the methods and/or techniques described herein.

The I/O units 222 of the controller 104 may include a single I/O component or more than one input-output component each working individually or with one another to interface with one or more devices or users. Example I/O units 222 may be or may include any suitable types of communication hardware or software including, but not limited to, communication ports configured to communicate with the optical fiber-based sensor system 106 or other suitable computing devices or systems. Example types of I/O units 222 may include wired communication components (e.g., HDMI components, Ethernet components, VGA components, serial communication components, parallel communication components, component video ports, S-video components, composite audio/video components, DVI components, USB components, optical communication components, and/or other suitable wired communication components), wireless communication components (e.g., radio frequency (RF) components, Low-Energy BLUETOOTH protocol components, BLUETOOH protocol components, Near-Field Communication (NFC) protocol components, WI-FI protocol components, optical communication components, ZIGBEE protocol components, and/or other suitable wireless communication components), and/or other suitable I/O units 222.

The user interface 216 may be a set of one or more physical or virtual components configured to communicate with the controller 104 or the optical fiber-based sensor system 106 via one or more wired or wireless connections. The user interface 216 may include one or more display devices 223, one or more I/O components 225, or one or more other suitable features or components.

The display device 223 may include any suitable display. Example suitable displays include, but are not limited to, touch screen displays, non-touch screen displays, liquid crystal display (LCD) screens, light emitting diode (LED) displays, head mounted displays, virtual reality displays, augmented reality displays, and/or other suitable display types.

The I/O components 225 may be and/or may include any suitable components or features for receiving user input via the user interface 216 or providing output via the user interface 216. Example input device(s) of the I/O components 225 may include, but are not limited to, touch screens, keypads, mice, touch pads, microphones, selectable buttons, selectable knobs, optical inputs, cameras, gesture sensors, eye trackers, voice recognition controls (e.g., microphones coupled to appropriate natural language processing components) and/or other suitable input devices. Example output device(s) of the I/O components 225 may include, but are not limited to, displays, speakers, vibration systems, tactile feedback systems, optical outputs, and/or other suitable output devices.

Figure 3:
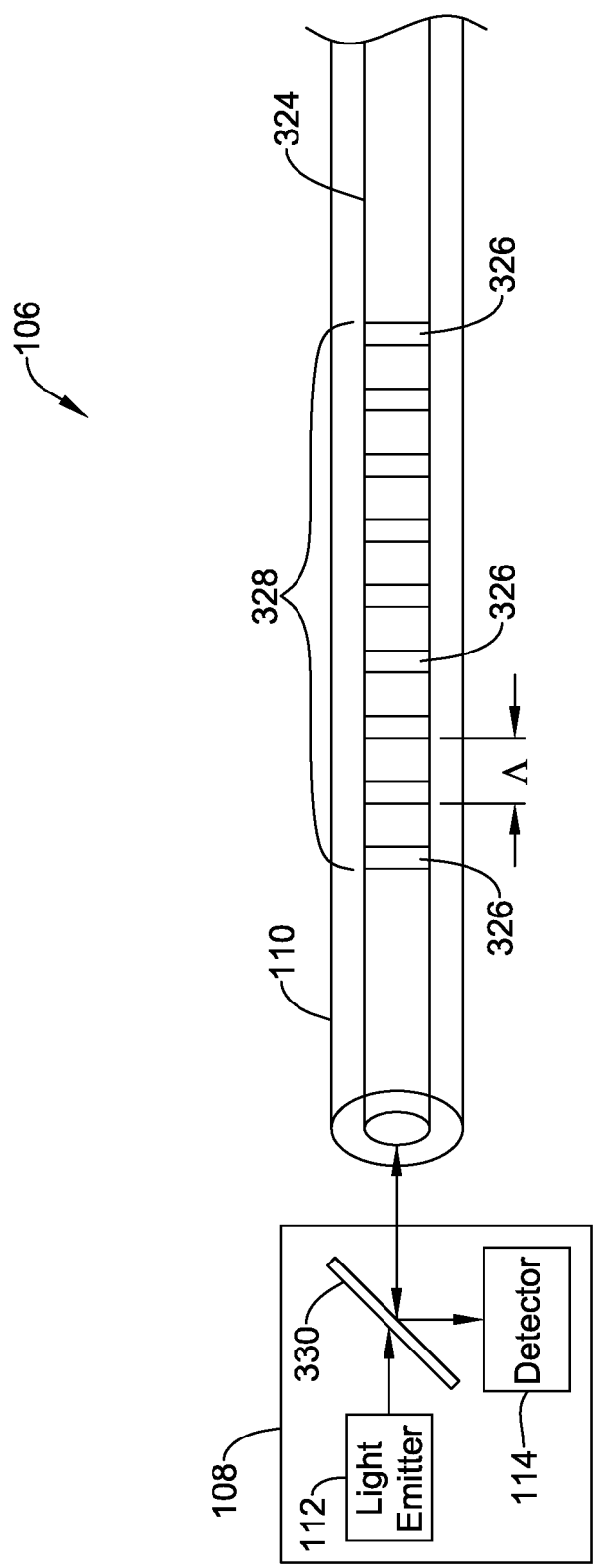
FIG. 3 is a schematic diagram of components of an illustrative optical fiber-based sensor system.

FIG. 3 depicts a schematic illustration of an illustrative configuration of the optical fiber-based sensor system 106. The system 106 includes the fiber optic cable 110 having one or more fiber cores 324, which may be optically coupled to the interrogator 108. The fiber core 324 may include one or more FBGs 326 (not all FBGs are labeled for clarity purposes) at a sensing area 328 (e.g., a sensing portion) extending along a longitudinal length at one or more desired locations of the fiber optic cable 110. When the optical fiber-based sensing system 106 is implemented in a surgical device (e.g., the surgical device 102), one or more sensing areas 328 may be located at or proximate to locations along the surgical device at which it is desirable to know a force acting thereon (e.g., where the force acting thereon is or is indicative of a force or pressure applied to anatomy of a patient by the surgical device proximate to the sensing area).

FIG. 3 is a schematic illustration, and does not necessarily depict all of the technical features of a fiber optic cable with FBGs, as would be understood by one of ordinary skill in the art. For example, the fiber optic cable 110 may include a core, cladding, and any other suitable layers, such as a buffer coating, protective housing, etc. Moreover, FBGs of the present disclosure, such as FBG 326 of fiber optic cable 110, may be formed by any suitable method, such as via two-beam interference, phase or photo masking, point-by-point writing by laser, and so on.

A length of a single period of the FBGs 326 (e.g., the grating structure), known as grating period or grating pitch A, may be any suitable distance. In some cases, the grating pitch A of the FBGs 326 may be within a range of about 0.5 μm and 20 mm. Further, the grating pitch A of the FBGs 326 may be consistent throughout all of the FBGs 326 or one or more grating pitches A may be different than one or more other grating pitches A of the FBGs 326. In some cases, the fiber optic cable 110 may include a fiber core 324 having FBGs 326 in which a grating pitch A at a distal end of the FBGs 326 may be shorter than a grating pitch A at a proximal end of the FBGs 326. In one example of a fiber optic cable 110, the fiber optic cable 110 may include a fiber core 324 having at least one sensing area 328 with 25 FBGs 326 at which a distal-most grating pitch A is 1 mm and all other grating pitches A are 10 mm. Other suitable configurations of FBGs 326 at the sensing area(s) 328 of the fiber optic cables 110 are contemplated.

The sensing area 328 may have any suitable length. In one example, the sensing area 328 may have a length in a range of 1 inch to 10 inches. In another example, the sensing area 328 may have a length in a range of 3 inches to 9 inches.

Further, the sensing area 328 may have any suitable number of FBGs. In one example, the sensing area 328 may have between 1 and 30 FBGs or more. In another example, the sensing area 328 may have up to 25 FBGs 326.

Multiple FBGs 326 and sensing areas 328 may be manufactured on a single optical fiber such that each FBG 326 or sensing area 328 may have a unique reflection wavelength. Such wavelength division multiplexing makes it possible to differentiate between reflection signals from a plurality of FBGs 326 or sensing areas 328 on a single fiber optic cable 110. To avoid ambiguity in interpreting FBG reflection signals, it may be desirable to fabricate each FBG 326 or each sensing area 328 to reflect within its own dedicated wavelength band wide enough to accommodate physically-induced reflection wavelength shifts (that encode signal information) as well as the intrinsic non-zero width of the non-shifted reflection distribution. Typically, FBG strain sensors may be allocated an approximately 5 nm wide range. Wider or narrower ranges may be employed, as appropriate. The FBGs 326 or the sensing areas 328 having unique reflection wavelengths may be formed at distinct/desired locations along the fiber optic cable 110, such that each particular reflected wavelength may then correspond to a specific sensor location along the length of the fiber optic cable 110.

The interrogator 108, which may be optically coupled to the fiber optic cable 110, may be configured to transmit light into the fiber optic cable 110 and to detect light reflected from the one or more FBGs 326. The resultant detected light reflected from the one or more FBGs 326 may encode local strain or force at each of the one or more FBGs 326 or sensing areas 328. More specifically, the interrogator 108 may be employed to measure the wavelength reflected by the FBGs 326 or sensing area 328 of the fiber optic cable 110. Further, the interrogator 110 may include any suitable light emitter 112 (e.g., as discussed above with respect to the light emitter 112), which may transmit light into the fiber core 324 via an optical coupler 330. While the optical coupler 330 is illustrated schematically to suggest a partially-reflective mirror or beam-splitter, any suitable optical coupler may be employed.

In an illustrative configuration, light may propagate down the fiber optic cable 110 and is selectively reflected by one or more FBGs 326 at their specific reflection wavelengths. The specific reflection wavelengths may encode or establish information about conditions at the FBGs 326 or sensing area 328 along the fiber optic cable 110, such as a pressure acting on the fiber core 324. Reflected light, obtained thereafter, returns to the interrogator 108, where the optical coupler 330 may direct the reflected light to a detector 114. Detection of light reflected by FBGs 326 or sensing areas 328, which may include determining reflection wavelengths, may then be interpreted by other components (not shown) of the interrogator 108 (or external to the interrogator 108, such as a local or remote controller) in order to arrive at measurements sensed by the FBGs 326 or sensing areas 328 (or calculations related to the measurements).

As discussed herein, an optical fiber-based sensing system (e.g. the optical fiber-based sensor systems 106 or other suitable optical fiber-based sensing system) may be implemented in or with various medical or surgical devices or instruments (e.g., surgical devices 102 or other suitable surgical devices). FIGS. 4-12 depict illustrative medical or surgical devices or instruments 102 in or with which such optical fiber-based sensing systems 106 may be implemented.

Figure 4:
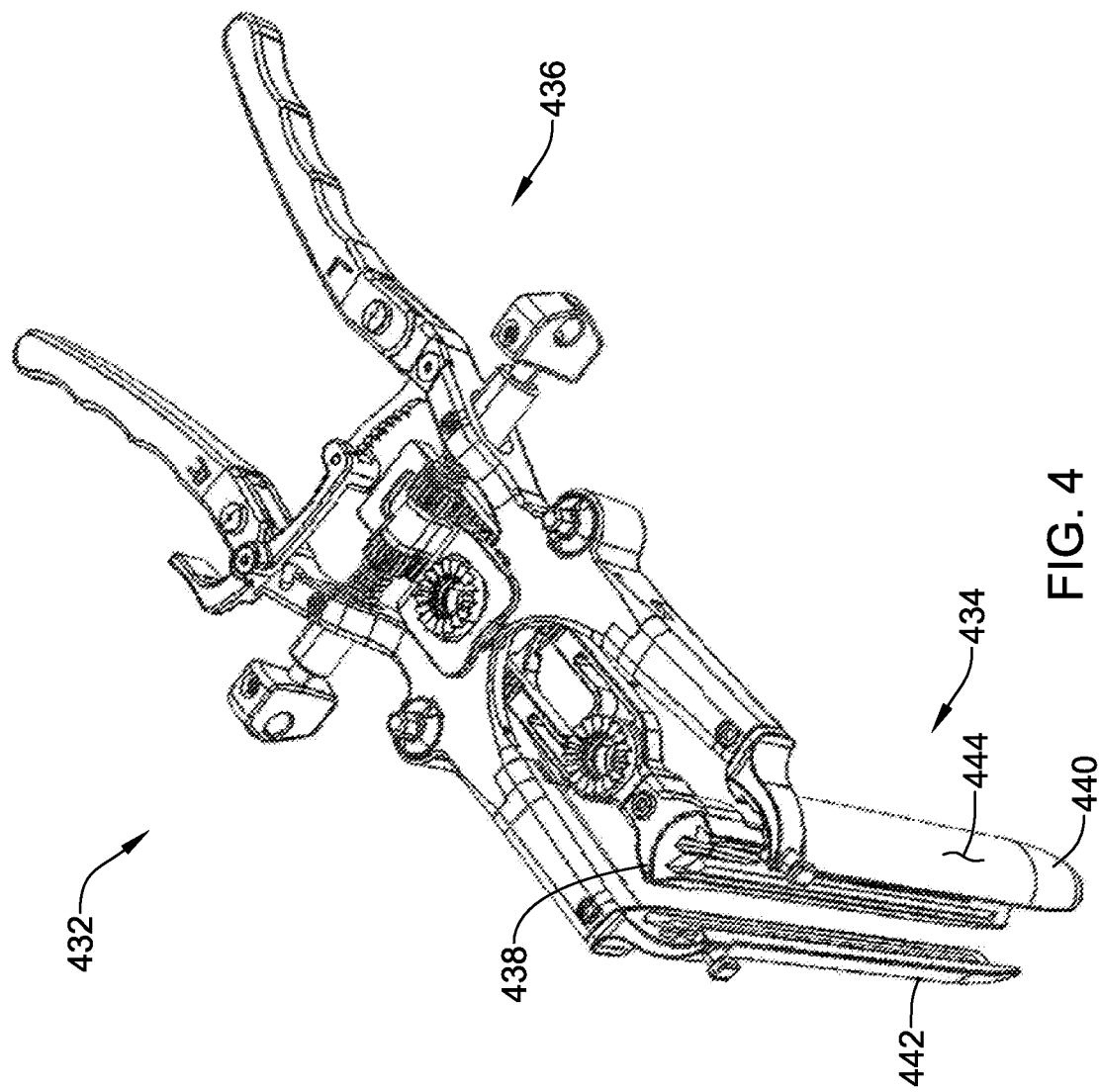
FIG. 4 is a schematic perspective view of an illustrative tissue retraction assembly.

FIG. 4 depicts a schematic perspective view of a tissue retraction assembly 432 that may be a surgical instrument or device 102 that may benefit from techniques described herein. The tissue retraction assembly 432 (e.g., a retractor) may form part of a surgical access system and may be used to create or enlarge a surgical site (e.g., a surgical corridor). Example tissue retraction assemblies 432 are described in U.S. Pat. No. 9,655,505, filed on Feb. 6, 2013 and titled SYSTEMS AND METHODS FOR PERFORMING NEUROPHYSIOLOGIC MONITORING DURING SPINE SURGERY, which is hereby incorporated by reference in its entirety for any and all purposes.

The tissue retraction assembly 432 may include one or more retraction blades 434 (e.g., retractor blades) extending from a body or a handle assembly 436. As depicted in FIG. 4, the tissue retraction assembly 432 may include a center retraction blade 438 (e.g., a retractor blade), a first side retraction blade 440, and a second side retraction blade 442, or other suitable combination of retractor blades. FIG. 4 depicts the retraction blades 434 in a partially open configuration, where outer surfaces 444 (e.g., where each retraction blade 434 may include an outer surface 444) are configured to interact with or contact tissue of a patient by applying radially outward forces to the anatomy to enlarge a surgical site within the retraction blades 434. Although the outer surfaces 444 may be rigid enough to enlarge a surgical site by applying a force to tissue, the outer surfaces 444 or at least a portion thereof may be responsive to forces acting on the outer surfaces 444 when contacting patient tissue such that the forces may be measured through the outer surfaces 444 using an optical fiber-based sensor system.

The retraction blades 434 may be formed from any material suitable for introduction into the human body. Example materials include, but are not limited to, aluminum, stainless steel, titanium, polycarbonate (e.g., clear polycarbonate or other suitable polycarbonate), polyether ether ketone (PEEK), polyphenylsulfone (PPSU), RADEL™, other suitable materials, or combinations of materials. Further, the retraction blade 434 may be optionally coated with a carbon fiber reinforced coating or other suitable coating to increase strength and durability.

Figure 5:
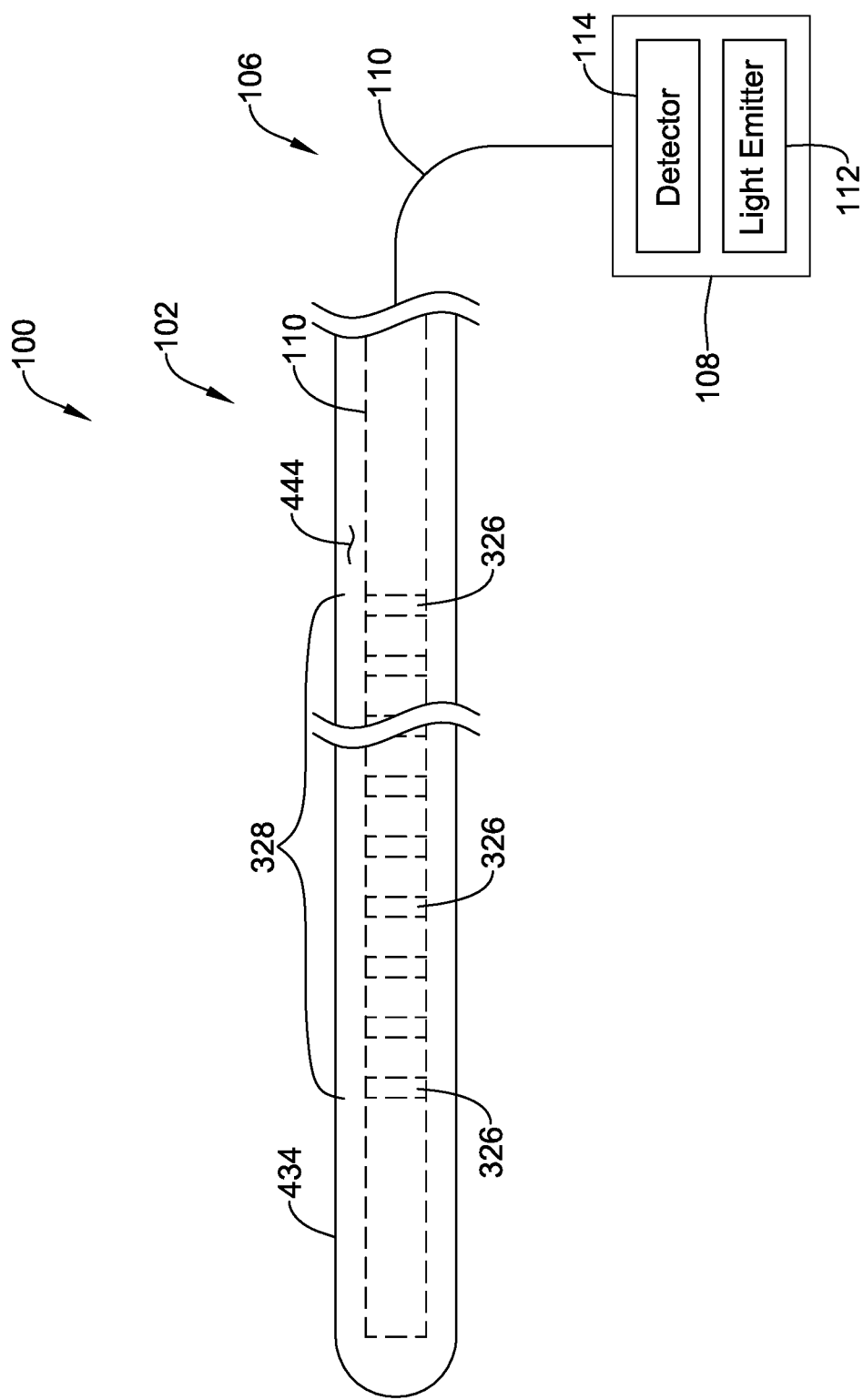
FIG. 5 is a schematic view of an illustrative system for sensing loads applied to a surgical device.

FIG. 5 depicts the illustrative surgical system 100 having the surgical instrument or device 102 and the optical fiber-based sensing system 106, where the surgical instrument or device 102 may be a tissue retraction assembly (e.g., the tissue retraction assembly 432 or other suitable tissue retraction assembly).

The optical fiber-based sensing system 106 may include the interrogator 108 optically coupled to the fiber optic cable 110. Among other components, the interrogator 108 may include the light emitter 112 configured to provide light to and through the fiber optic cable 110 and the light detector 114 configured to sense or detect light reflected back through the fiber optic cable 110 to the interrogator 108. In some cases, the fiber optic cable 110 may include FBGs 326.

As depicted in FIG. 5, the retraction blade 434 incorporates the fiber optic cable 110, which is shown in broken lines. The fiber optic cable 110 may be positioned with respect to the retraction blade 434 such that the sensing area 328 including one or more FBGs 326 is positioned along the retraction blade 434 to allow the optical fiber-based sensing system 106 to sense forces acting on the outer surface 444 of the retraction blade 434 and determine or infer an amount force being applied to a patient's anatomy by the outer surface 444.

The fiber optic cable 110 may be positioned in or otherwise along the retraction blade 434 (e.g., a tissue contacting component) adjacent a portion of the retraction blade 434 responsive to forces acting thereon (e.g., the outer surface 444) in any suitable manner such that the fiber optic cable 110 may mechanically deform in response to force acting on the retraction blade 434 to facilitate measuring the forces applied thereto. In some cases, the fiber optic cable 110 may be permanently positioned in or along the retraction blade 434 or the fiber optic cable 110 may be removably positioned in or along the retraction blade 434. In one example, the fiber optic cable 110 may be embedded in the retraction blade 434 at the time of forming the retraction blade 434. In another example, a channel may be formed in the retraction blade 434 either at the time of forming the retraction blade or at a later time and the fiber optic cable 110 may be permanently or removably threaded through or otherwise disposed within the channel. In some cases, when inserted in the channel and not permanently secured therein, the fiber optic cable 110 may be withdrawn from the channel after desired measurements are taken. In a further example, the retraction blade 434 may be three-dimensionally (3D) printed to include a channel and the fiber optic cable 110 may be snaked or otherwise inserted through the channel in the retraction blade 434 such that the sensing area 328 of the fiber optic cable 110 extends along a portion of the retraction blade at which strain or force is to be sensed.

The channel, when formed, may be any suitable size. In some cases, the channel may have a cross-sectional diameter in a range of about $1/64$ of an inch to about $1/16$ of an inch, but other diameters are contemplated. In one example, the channel may have a diameter of $1/32$ of an inch, but this is not required.

When the fiber optic cable 110 is permanently positioned (e.g., secured via adhesive, over molding, or another technique configured to resist non-destructive removal of the fiber optic cable 110) within the retraction blade 434 or other surgical or medical device or instrument 102, a proximal end of the fiber optic cable 110 may include an optical connector (not shown). The optical connector, when included, may be configured to optically connect to the interrogator 108 or a further optical connector extending from the interrogator 108. The optical connectors may be configured to mate in any suitable manner.

Although FIG. 5 depicts a relatively straight fiber optic cable 110 extending through or otherwise along the retraction blade 434, the fiber optic cable 110 (or a channel in the retraction blade 434) may be positioned in one or more other suitable patterns. Example patterns include, but are not limited to, straight lines, a U-shape (e.g., with a rounded base of the U-shape positioned adjacent a distal end of the retraction blade 434), an S-shape (e.g., a repeating S-shape along a length of the retraction blade 434), other suitable patterns, or combinations of patterns. Such patterns can be selected to enhance the ability of useful data to be obtained.

In one illustrative example configuration of the retraction blade 434 incorporating the fiber optic cable 110 having the sensing area 328, the retraction blade 434 may be formed via 3D printing with a channel having a diameter of about $1/32$ of an inch. The fiber optic cable 110 may then be threaded through the channel such that at least one sensing area 328 extends along a desired location of the retraction blade 434. In an illustrative instance when the blade has a length of about 4.25 inches and the pattern of the channel or resulting fiber optic cable 110 threaded through the channel is U-shaped, the sensing area 328 of the fiber optic cable 110 may be about 8.5 inches in length with 25 FBGs 326, wherein the distal most grating period or pitch A is or is about 1 mm and the other grating periods or pitch is about 10 mm.

Figure 6:
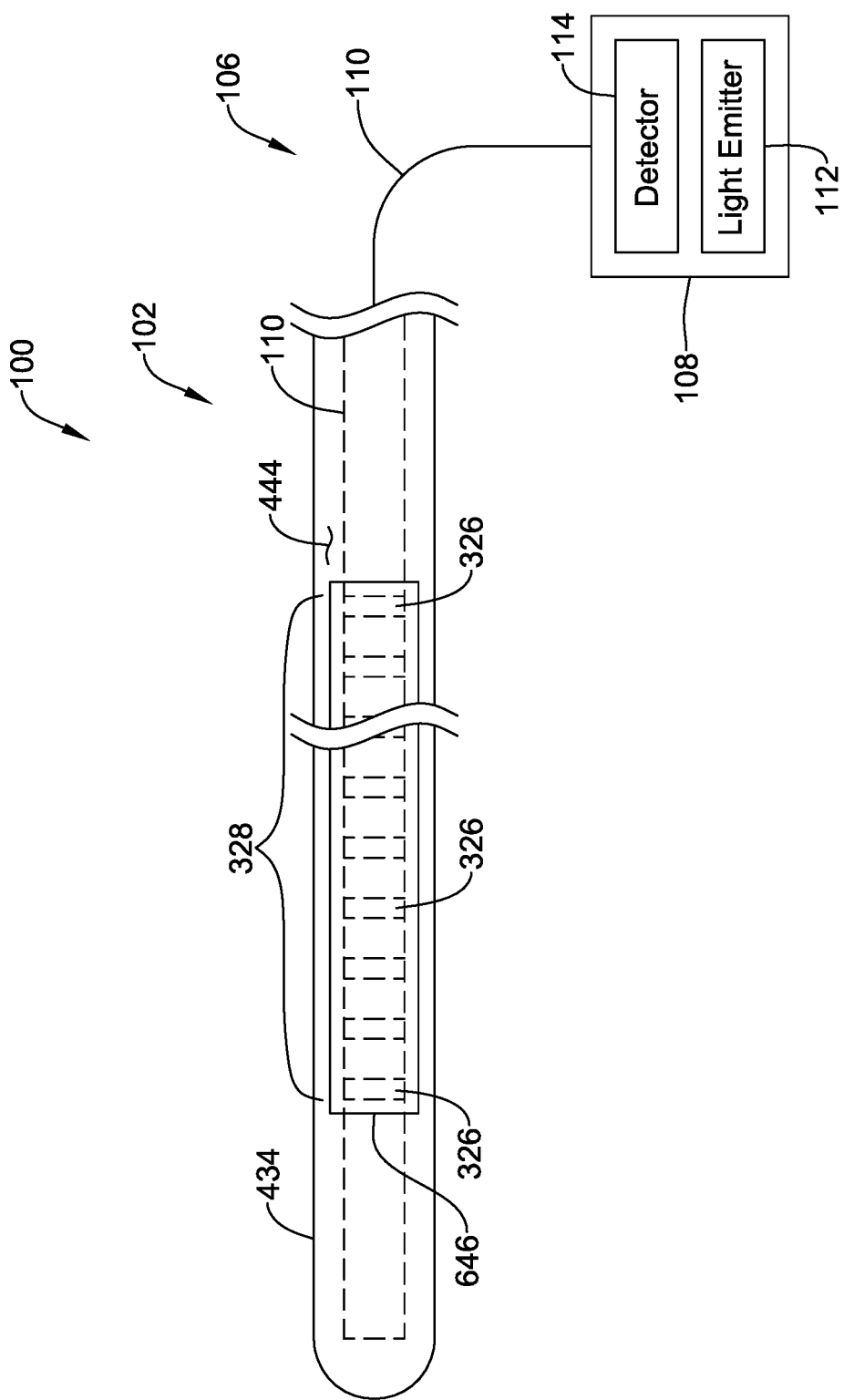
FIG. 6 is a schematic view of an illustrative system for sensing loads applied to a surgical device.

FIG. 6 depicts the illustrative surgical system 100 having the surgical instrument or device 102 and the optical fiber-based sensing system 106, where the surgical instrument or device 102 may be a tissue retraction assembly (e.g., the tissue retraction assembly 432 or other suitable tissue retraction assembly). As depicted in FIG. 6, the retraction blade 434 of the surgical instrument or device 102 is depicted as incorporating a sensing portion 646 and the fiber optic cable 110, which is shown in broken lines. The portion of the fiber optic cable 110 in the retraction blade 434 may include the sensing area 328 having one or more FBGs 326.

The sensing portion 646 may facilitate transferring forces acting on the outer surface 444 of the retraction blade 434. In some cases, the sensing portion 646 of the retraction blade 434 may include a first material that may extend between or at least partly between the fiber optic cable 110 extending along the retraction blade 434 and the outer surface 444 of the retraction blade 434 and at least another portion of the retraction blade 434 defining the outer surface 444 may include a second material. In some cases, the first material may be more responsive to forces acting on the outer surface 444 of the retraction blade (e.g., may be more flexible or less rigid) than the second material, such that forces acting on the retraction blade 434 may be accurately and sufficiently transferred to the sensing area 328 of the fiber optic cable 110 while the retraction blade 434 maintains sufficient rigidity to retract patient tissue at a surgical site. Examples types of the first material more responsive to forces acting thereon than the second material may include, but is not limited to polyphenylsulfone (PPSU, such as RADEL by SOLVAY of Brussels, Belgium), polycarbonate, other suitable materials or combinations thereof. Example types of the second material less responsive to forces acting thereon than the first material may include, but is not limited to, aluminum, stainless steel, titanium, other suitable materials, or combinations thereof.

Figure 7:
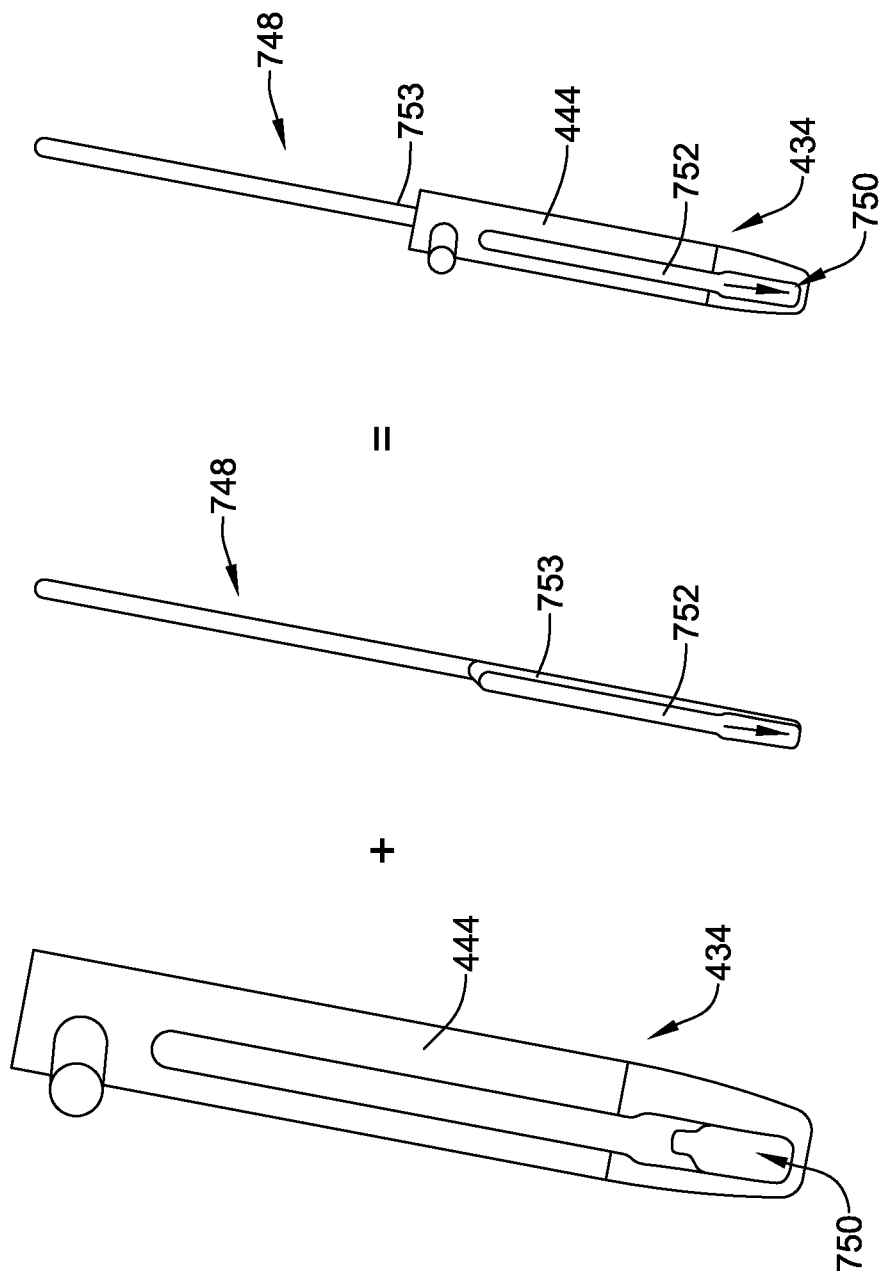
FIG. 7 is a schematic view of an illustrative retraction blade including a removable body.

FIG. 7 depicts an illustrative configuration of the surgical instrument or device 102, where the surgical instrument or device 102 is a portion of a retraction assembly having the retraction blade 434 that includes a removable electrode component 748. The electrode component 748 may be disposable, but this is not required. Example electrode components are described in U.S. Pat. No. 9,655,505, filed on Feb. 6, 2013 and titled SYSTEMS AND METHODS FOR PERFORMING NEUROPHYSIOLOGIC MONITORING DURING SPINE SURGERY, which was incorporated above in its entirety for any and all purposes.

The electrode component 748 may assist in detection of a depth or location of nerves relative to a length of the retraction blade 434 after or while the retraction assembly is placed by outputting electrical signals sent through a body, which can be directly or indirectly detected by a detector. The electrode component 748 may also assist in assessing a health and status of the nerves closest to the retraction blade 434. Using a disposable or removable electrode component 748 may permit the retraction blade 434 to be sterilized and reused endlessly without regard for degradation to the electrode component 748, which in turn ensures that results from nerve monitoring using the electrode component 748 are consistent and reduces potentially high costs of replacing the entire blade structure if the electrode component 748 were to degrade.

As depicted in FIG. 7, the retraction blade 434 may include an opening 750 through the outer surface 444 thereof. The electrode component 748 may be added to the retraction blade 434 by inserting a conductive portion 752 (e.g., an electrode) within a removable body 753 into the opening 750 through the outer surface 444 of the retraction blade 434, such that the conductive portion 752 of the electrode component 748 may form a portion of the outer surface 444.

The removable body 753 may have any suitable configuration and/or material properties. In some cases, the removable body 753 may be solid, rigid, flexible, or combinations thereof.

The removable body 753 may be formed from any material suitable for introduction into the human body. Example materials include, but are not limited to, PPSU, polycarbonate, other suitable materials or combinations thereof. In some cases, a material of the removable body 753 may be more responsive to forces acting thereon than a material of the retraction blade 434.

The electrode component 748 may be coupled to the retraction blade 434 in any suitable manner. Although not required, in one example the electrode component 748 may be slid into, snap fit into, or otherwise positioned in or coupled to the opening 750 and coupled to the retraction blade 434.

Figure 8:
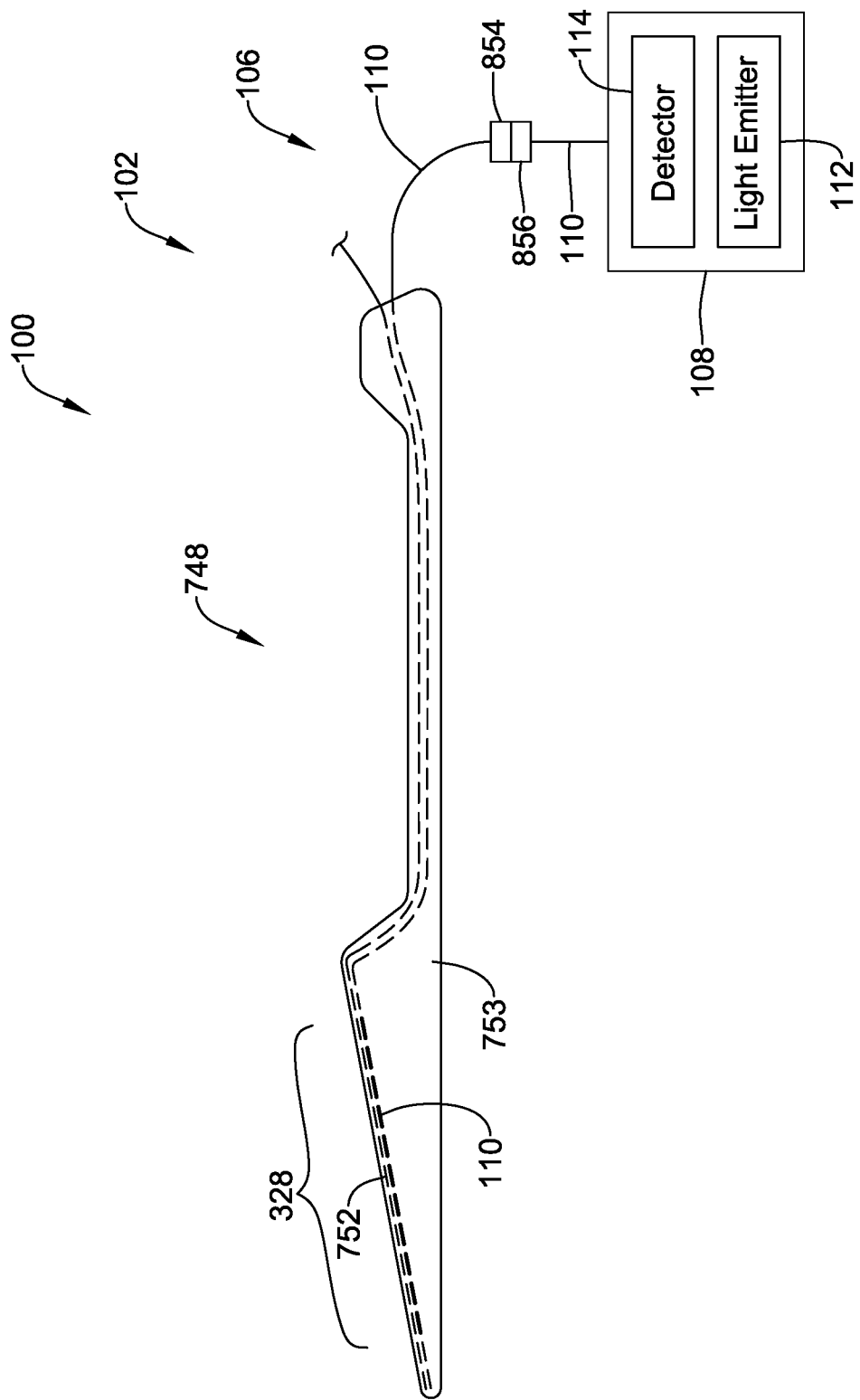
FIG. 8 is a schematic view of an illustrative system for sensing loads applied to a surgical device.

FIG. 8 depicts the surgical system 100 with a side view of an illustrative configuration of the electrode component 748 (e.g., the surgical device or instrument 102 or a portion thereof) in communication with the optical fiber-based sensing system 106. As depicted in FIG. 8, the fiber optic cable 110 may extend from an interrogator 108 to the electrode component 748, where a sensing area 328 may extend along or adjacent to the conductive portion 752 (e.g., the electrode) of the electrode component 748. The fiber optic cable 110 may be inserted or embedded into the electrode component 748 in a manner similar to or different than how an optical fiber may be inserted or embedded into other medical or surgical devices or instruments. Additionally or alternatively, the fiber optic cable 110 may be bonded to the electrode component 748 in any suitable manner including, but not limited to, an ultrasonic weld, adhesive, etc.

The bolded portion of the broken line representing the fiber optic cable 110 in FIG. 8 may represent a sensing portion 328 of the fiber optic cable 110 that may be configured to sense forces/strains acting on the electrode component 748. In such cases, the electrode component 748 may be formed from a housing material that is intended to be flexible or responsive to forces acting thereon such that material properties of the fiber optic cable 110 may be changed and allow forces acting on the electrode component 748 to be measured using the optical fiber-based sensing system 106.

Further, as the electrode component 748 may be disposable it may be desirable for the fiber optic cable 110 to extend through the electrode component 748 to be releasably coupled to the interrogator 108. As depicted in FIG. 8, a proximal end of the fiber optic cable 110 extending through the electrode component 748 may include a first connector 854 configured to optically couple or otherwise connect to a second connector 856 extending from the fiber optic cable 110 in communication with the interrogator 108. Such a connection technique may allow fiber optic cables 110 of replacement electrode components 748 to be coupled to the interrogator 108 after discarding a previous electrode component 748.

In one illustrative example configuration of the electrode component 748, the removable body 753 may incorporate the fiber optic cable 110 having the sensing area 328 and the conductive portion 752 (e.g., the electrode). In such a configuration, the fiber optic cable 110 may be bonded to, embedded in, or otherwise coupled to the removable body 753. The conductive portion 752 may have a thickness of about 0.055 inches, and a length of about 8.75 inches, but other configurations are contemplated. The sensing area 328 of the fiber optic cable 110 may be about 3.5 inches in length with 25 FBGs wherein the distal grating periods or pitch A is or is about 1 mm and the other grating periods or pitch is about 10 mm, but other configurations are contemplated.

Figure 9:
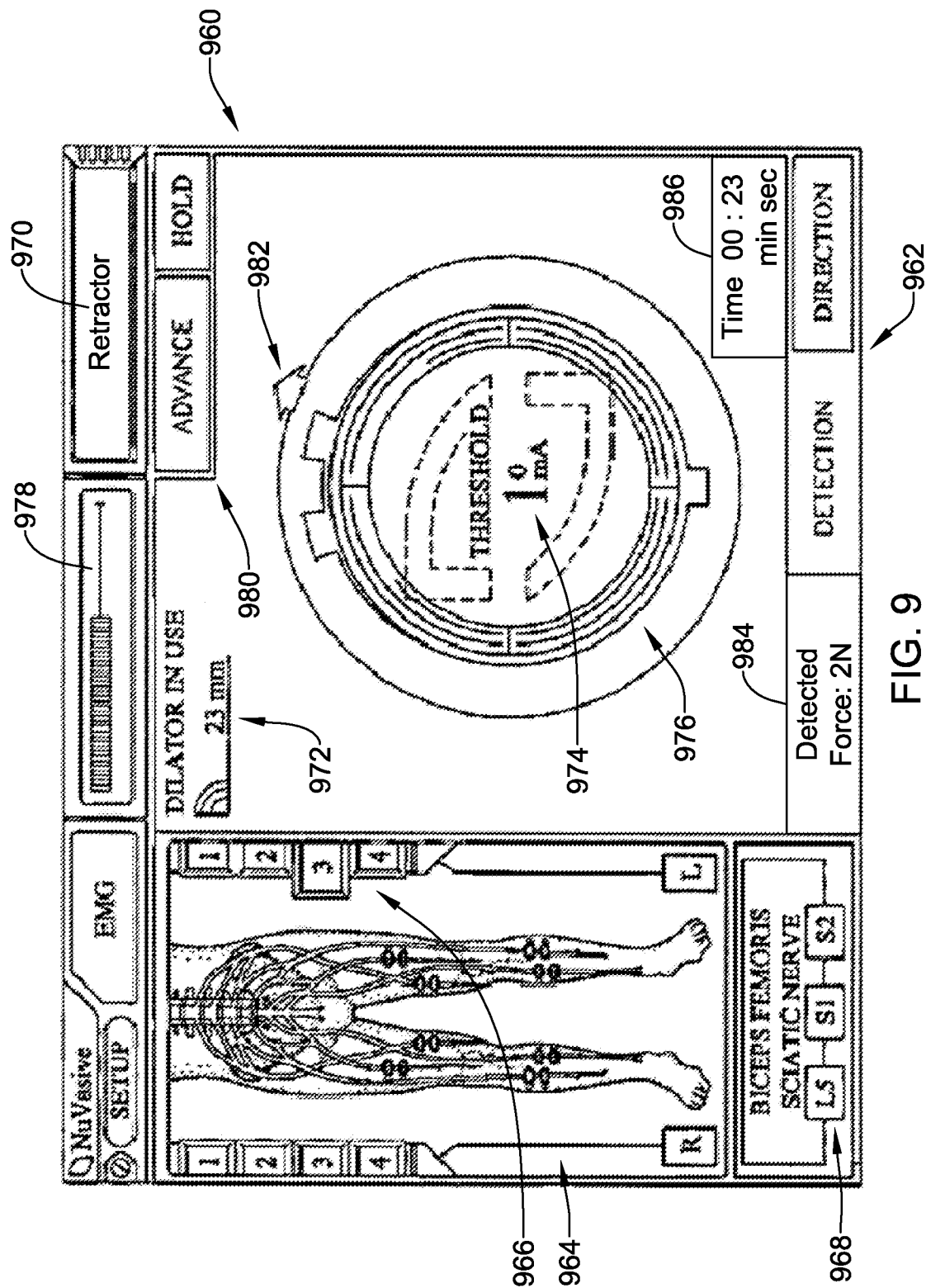
FIG. 9 is a schematic view of an illustrative screen display for a surgical monitoring system.

FIG. 9 is an illustrative screen 960 (e.g., to be displayed on a display 223 or user interface 216 discussed herein or other suitable display or user interface) illustrating one configuration of a nerve direction and force monitoring system. Example screens of a nerve monitoring system are described in U.S. Pat. No. 9,655,505, filed on Feb. 6, 2013 and titled SYSTEMS AND METHODS FOR PERFORMING NEUROPHYSIOLOGIC MONITORING DURING SPINE SURGERY, which was incorporated above in its entirety for any and all purposes.

The screen 960 may be intended to communicate a variety of information to the surgeon or others in a procedure room in an easy-to interpret fashion. Such information or other suitable information may be communicated in any number of suitable manners, including, but not limited to, the usage of visual indicia (e.g., alphanumeric characters, light-emitting elements, graphics, etc.) and audio communications (e.g., via a speaker). In one example, the information may include, but is not necessarily limited to, a display of the function 962 (e.g., in this case "DIRECTION" is selected), a graphical representation of a patient 964, a myotome level being monitored 966, a nerve or group associated with a displayed myotome 968, a name of an instrument being used 970 (e.g., a retractor), a size of the instrument being used 972, a stimulation threshold current 974, a graphical representation of the instrument being used 976 to provide a reference point from which to illustrative a relative direction from the instrument to a nerve, a stimulation current being applied to stimulation electrodes 978, instructions 980 for the user, an arrow 982 indicating a direction from the instrument to a nerve, a detected amount of force 984 applied to the instrument (e.g., from an optical fiber-based sensing system), an elapsed time 986 since a detected force has passed a threshold amount of force while nerve tissue has been detected, or other suitable information.

Figure 10:
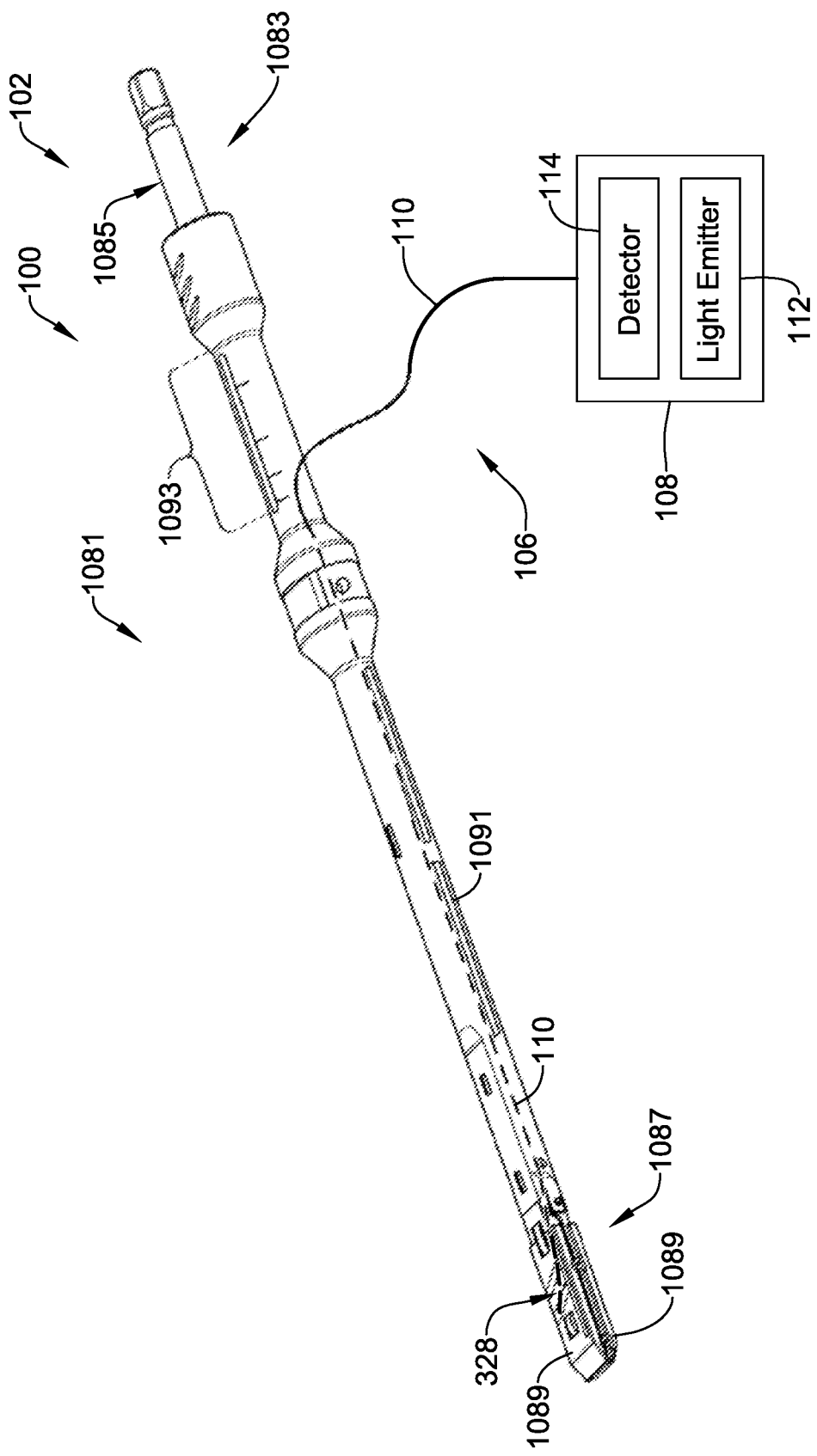
FIG. 10 is a schematic view of an illustrative system for sensing loads applied to a surgical device.

FIG. 10 depicts an illustrative surgical system 100 having a surgical instrument or device 102 and an optical fiber-based sensing system 106, where the surgical instrument or device 102 may be a measurement tool 1081. The measurement tool 1081 may be used for determining an approximate height or width required by an implant (e.g., a spinal implant or other suitable implant) upon insertion between vertebral bodies, or for other suitable purposes. Example measurement tools 1081 are described in U.S. Pat. No. 10,973,650, filed on Jul. 6, 2018 and titled LORDOTIC EXPANDABLE FUSION IMPLANT, which is hereby incorporated by reference in its entirety for any and all purposes.

The measurement tool 1081 may include a first end 1083 with a driver 1085 and a second end 1087 with two movable endplates 1089. Further, the measurement tool 1081 may include or be in communication with the optical fiber-based sensing system 106. The optical fiber-based sensing system 106 may include a fiber optic cable 110 extending from a sensing area 328 proximate a location of the measurement tool 1081 that may apply a force to anatomy of a patient (e.g., the endplates 1089) to a proximal location coupled to the interrogator 108.

The driver 1085 may be rotatable. As the driver 1085 rotates, its rotational movement may be translated by a series of linkages located in a shaft 1091 into a force that may expand the movable endplates 1089. The endplates 1089 may be attached to a series of arms which are in turn attached to the linkages and as the driver 1085 rotates, the endplates 1089 may be either raised away from the shaft 1091 or lowered towards the shaft 1091.

The sensing area 328 of the fiber optic cable 110 may be disposed at one or more locations, such as one or both of the endplates 1089 and one or more of the linkages. The sensing area 328 may be configured to provide an indication of the stress or strain present at the locations of the measurement tool 1081 proximate thereto. In some examples, the stress or strain may be used to directly or indirectly measure an amount of pressure or force being applied to the patient tissue (e.g., vertebrae) during measurement of a height required for an implant.

The measurement tool 1081 may further comprise an indicator feature 1093. As the endplates 1089 are inserted between vertebral bodies in their collapsed configuration, the indicator feature 1093 may have a marker correlating the height of the endplates 1089 in the collapsed position to position "1" and as the endplates 1089 are moved into their expanded configuration by the rotation of the driver 1085, the marker may move from position "1" to position "2", "3", etc. The position numbers may then be correlated with an actuation height (e.g., separation) of the endplates 1089 providing a user of the measurement tool 1081 an estimate of a height of a needed implant for a particular patient's anatomy, which may then be associated with force applied to the vertebral bodies at the required height.

Figure 11:
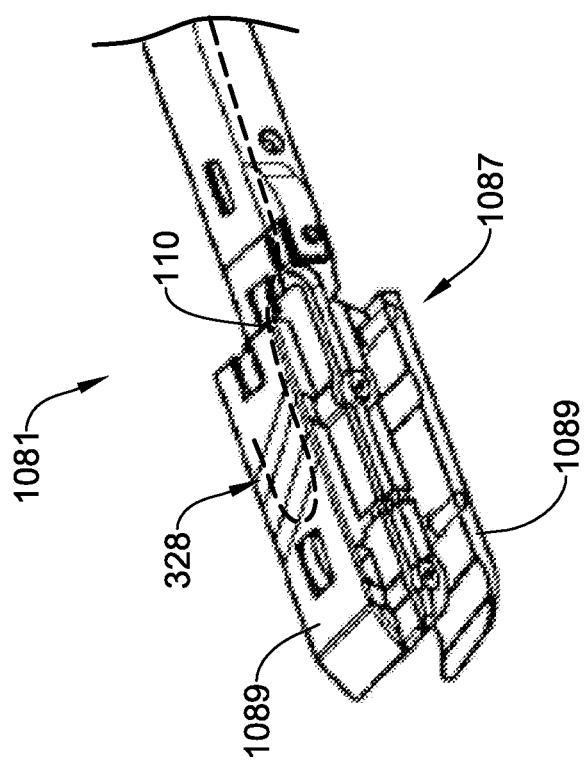
FIG. 11 is a schematic view of a distal portion of an illustrative measuring tool depicted in FIG. 10.

FIG. 11 depicts an enlarged perspective view of the second end 1087 of the measurement tool 1081, at which the endplates 1089 have been expanded. Although the sensing area 328 of the fiber optic cable 110 extending through the measurement tool 1081 is depicted proximate only a single endplate 1089, it is contemplated that the fiber optic cable 110 may include more than one optical core having a sensing area and a second optical core may extend to a second endplate 1089 such that the sensing area of the second optical core is able to sense forces or strains acting on the second endplate 1089.

Figure 12:
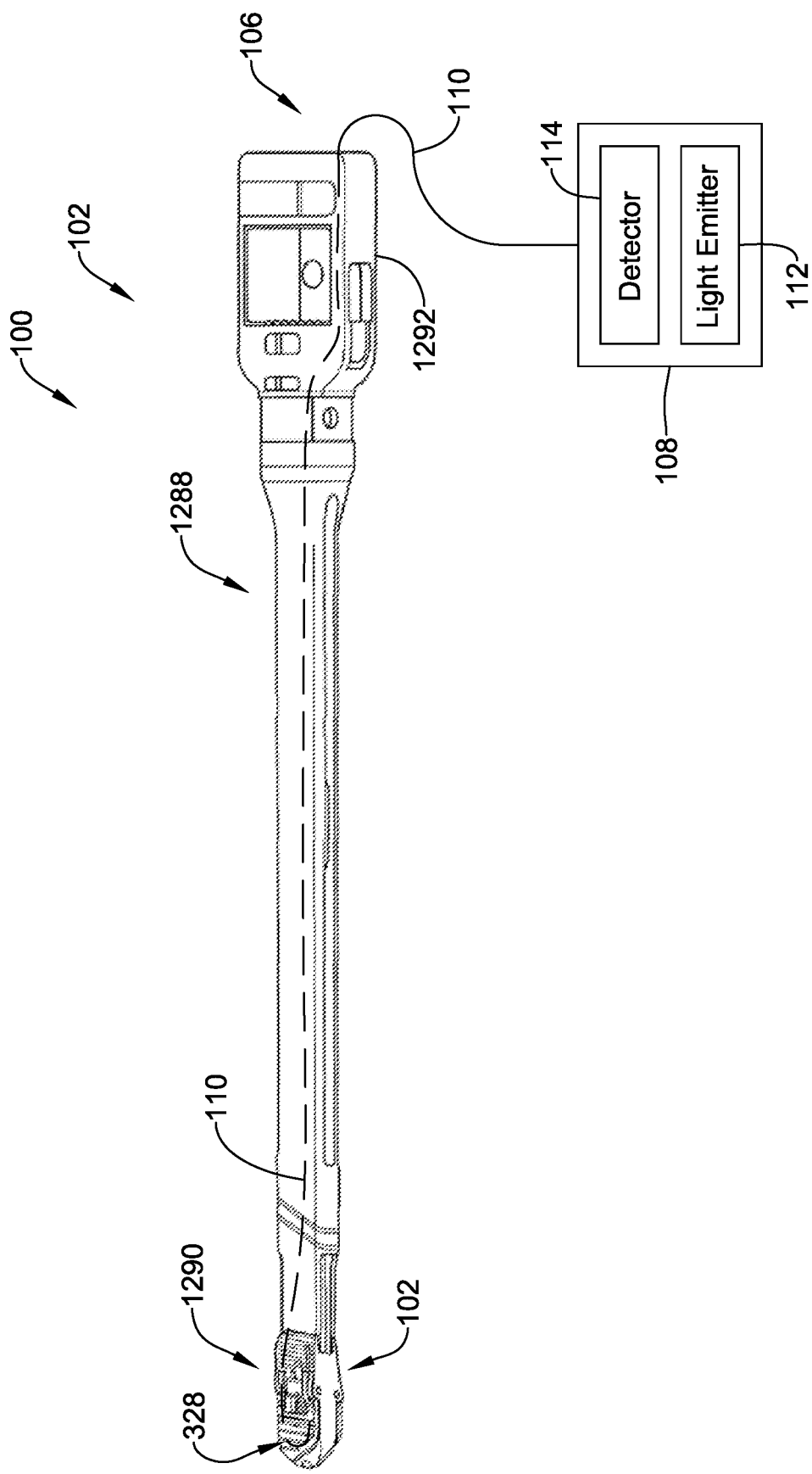
FIG. 12 is a schematic view of an illustrative system for sensing loads applied to a surgical device.

FIG. 12 depicts an illustrative surgical system 100 having a surgical instrument or device 102 and an optical fiber-based sensing system 106, where the surgical instrument or device 102 may be an insertion tool 1288 that may include or engage with an implant 1290. In some cases, the insertion tool 1288 may engage with the implant 1290 during a spinal surgery. Example insertion tools and implants are described in U.S. Pat. No. 10,973,650, filed on Jul. 6, 2018 and titled LORDOTIC EXPANDABLE FUSION IMPLANT, which was previously incorporated by reference in its entirety for any and all purposes; U.S. Pat. No. 9,687,357 filed on Feb. 10, 2014 and titled VERTEBRAL BODY REPLACEMENT, which is incorporated by reference in its entirety for any and all purposes; U.S. Pat. No. 10,350,084 filed on Sep. 14, 2016 and titled EXPANDABLE SPINAL FUSION IMPLANT, RELATED INSTRUMENTS AND METHODS, which is incorporated by reference in its entirety for any and all purposes; and U.S. Pat. No. 9,795,493 filed on Mar. 17, 2014 and titled EXPANDABL INVERTEBRAL IMPLANT AND METHOD OF USE THEREOF, which is incorporated by reference in its entirety for any and all purposes. A trial implant, which may be a component used to test a site for an implant, may be similar to or different than the implants 1290 discussed herein and may be coupled to the insertion tools 1288 in a manner similar to the implants 1290.

The insertion tool 1288 may include a rotatable element 1292 at a proximal end of the insertion tool 1288 opposite a distal end at which the implant 1290 may be located. The rotatable element 1292 may be in communication with the implant 1290 such that as the rotatable element 1292 is rotated by a user, endplates of the implant 1290 may be adjusted to secure the implant 1290 between vertebral bodies of a patient.

The fiber optic cable 110 may extend through the insertion tool 1288 and into the implant 1290 such that the sensing area 328 may extend along one or more endplates of the implant that are configured to separate from one another and contact vertebral bodies of a patient. Such a configuration may allow a user of the system 100 to better understand the forces acting on the patient's body when an implant is inserted. Although not shown, the fiber optic cable 110 extending into the implant 1290 may be slidably removable from the implant 1290 or optically coupled via one or more connectors adjacent a connection between the implant 1290 and the insertion tool 1288.

Figure 13:
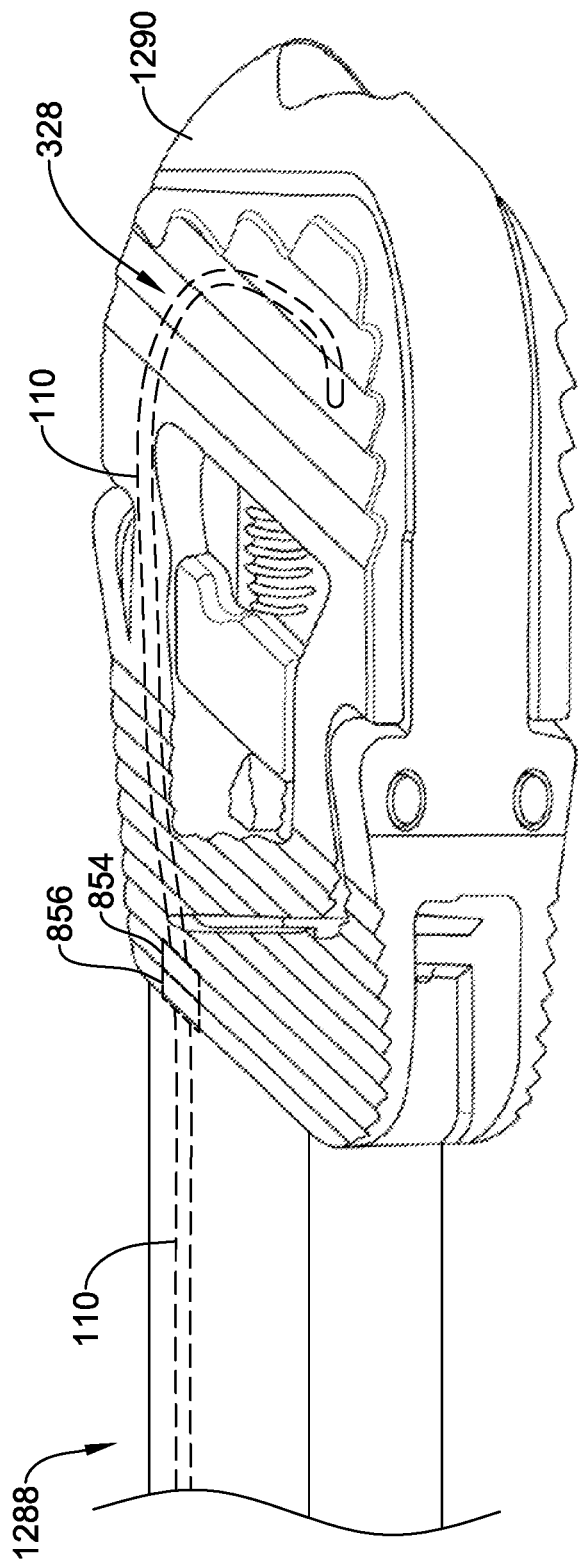
FIG. 13 is a schematic view of a distal portion of an illustrative insertion tool connected to an illustrative implant depicted in FIG. 12.

FIG. 13 depicts an enlarged perspective view of the implant 1290 connected to the insertion tool 1288. Although the sensing area 328 of the fiber optic cable 110 extending through the insertion tool 1288 is depicted proximate only a single side of the implant 1290, it is contemplated that the fiber optic cable 110 may include more than one optical core having a sensing area and a second optical core may extend to a second side or other side of the implant 1290 such that a sensing area of the second optical core is able to sense forces or strains acting on the second or other side of the implant 1290.

To facilitate use of the fiber optic cable 110 in an implant 1290 that stays within a patient after implanting, the fiber optic cable 110 within the implant 1290 may include a first connector 854 at a proximal end thereof that may be configured to optically couple or otherwise connect to a second connector 856 at a distal end of the fiber optic cable 110 extending through the insertion tool 1288. The first and second connectors 854, 856 may be decoupled when the insertion tool 1288 is decoupled from the implant 1290.

Alternatively or additionally to including the first and second connectors 854, 856, the fiber optic cable 110 may be configured to be severed such that a portion of the fiber optic cable 110 may remain in the implant 1290 after implantation. For instance, a portion of the of the fiber optic cable 110 can be weakened or otherwise configured to be broken off (e.g., upon disconnection of the insertion tool 1288 and the implant 1290). In some instances, the insertion tool 1288 can include a cutter (e.g., sharpened surface) or other component configured to sever the fiber optic cable 110 (e.g., in a same or separate step from the step that causes the insertion tool 1288 to deploy or disconnect the implant 1290).

In some cases, the sensed measurements using the optical fiber-based sensing system 106 may be used to determine an extent to which the expandable implant or trial implant is expanded. Such determination may be used with or as an alternative to a height indicator feature (e.g., the indicator feature 1093 or other suitable indicator feature). The sensed measurements using the optical fiber-based sensing system 106 may be used to determine an extent an implant or trial implant expands in length or width in addition to or as an alternative to height. For example, the sensed measurements can be used to determine an amount of force applied by the expandable implant or trial at the height and such a determination may be used to facilitate the determination of an appropriate height (e.g., beyond a surgeon's subjective feel of appropriate size or force applied).

In operation, when an expected amount of force acting on the implant 1290 is known for different expansion amounts of the expandable implant 1290, it may be possible to track a position of the inserter or the expandable implant 1290 throughout the process of inserting and placing the implant 1290. For example, based on the sensed forces, a position of the expandable implant 1290 in a disc space between two vertebrae may be determined. Further, knowing the positioning of the implant may allow users and or systems to correlate tactile feel or feedback and force readings to better understand how the expandable implant 1290 should be further manipulated, if at all, to achieve a desired positioning in the disc space.

Figure 14:
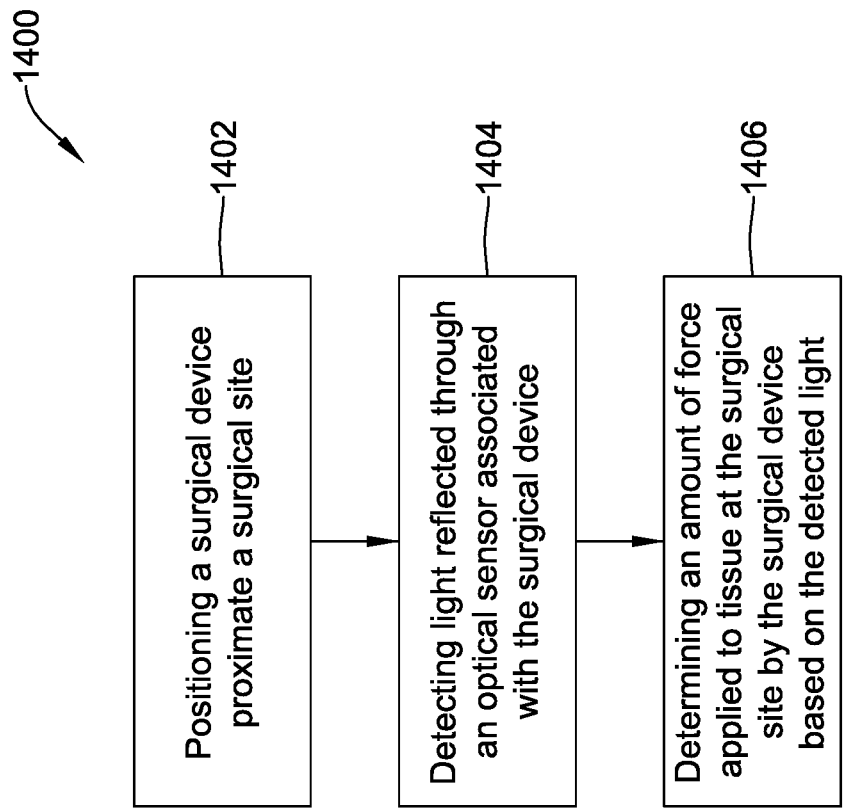
FIG. 14 is a schematic diagram of an illustrative method.

FIG. 14 depicts a box diagram of an illustrative method 1400 of determining an amount of force applied to tissue at or adjacent a surgical site by a surgical device. Determining an amount of force applied to tissue proximate to a surgical site may facilitate a user (e.g., a surgeon or other user) in identifying how a surgical action may affect the patient (e.g., how retraction of tissue may apply an amount of force to a nerve), identifying a size of an implant to be used in a procedure, identifying when an implant has been fully inserted into the patient, etc.

The method 1400 may include positioning 1402 a surgical device or instrument 102 proximate a surgical site of a subject (e.g., a patient or other suitable subject). The surgical device or instrument 102 may be positioned at or proximate to the surgical site in any suitable manner such as by being inserted through a surgical access tube, via a surgical robot, via use of a surgical navigation tool, or inserted in one or more other suitable manners.

Any suitable surgical device may be positioned proximate the surgical site, including those discussed herein and other surgical devices. Example surgical devices include, but are not limited to, retractors used for expanding or maintain surgical sites, measurement tools and trial implants, insertion tools and implants, drills, drill bits, saws, bone saws, screws, or other suitable surgical device or implants.

Either as the surgical device 102 is being positioned at the surgical site or once the surgical device 102 is positioned at the surgical site, light reflected by or through an optical sensor associated with the surgical device 102 may be detected 1404. The optical sensor may be or may be part of the optical fiber-based sensor system 106, where a fiber optic cable 110 may extend from an interrogator 108 to a distal end portion of the surgical device 102 that is configured to be positioned proximate the surgical site. The fiber optic cable 110 may include a sensing area 328 having FBGs thereon at a location proximate the distal end portion or other portion of the surgical device 102. When so configured, the interrogator 108 may direct light through the fiber optic cable 110 and the sensing area 328 reflects light back to the interrogator 108 that is indicative of forces acting on the fiber optic cable 110 and thus, forces acting on the distal end portion of the surgical device 102. The wavelength of the light detected by the interrogator 108 may depend on a configuration of the FBGs at the sensing area when force or strain is applied thereto relative to when no force or strain is applied thereto.

Once reflected light has been detected by the interrogator 108, an amount of force that is applied to tissue of the patient at or adjacent (e.g., proximate to) the surgical site by the surgical device 102 may be determined 1406 based on the detected light that has been reflected through the fiber optic cable 110. In some cases, detecting light may include determining a wavelength of light detected and translating that information into usable data which may then be compared to a wavelength when no force or strain is applied to the sensing area 328 of the fiber optic cable 110 to determine a relative force applied to the fiber optic cable 110. Through known relationship, an estimate of an amount of force or pressure applied to a patient's anatomy through the surgical device 102 may be determined based on the forced applied to the fiber optic cable 110.

Determining a force or pressure applied to a patient's tissue by the surgical device 102 may facilitate a user taking an action in real time during surgery. For example, taking an action in real time may include viewing a force measurement during an implantation of an implant and using the force measurement to determine when or if the implant requires adjusting. In another example, taking an action in real time may include viewing a force measurement while developing a surgical site corridor and if a certain amount of force is realized relative to a nerve, adjusting the surgical device used to create the surgical site corridor to relieve the force on the nerve.

In some cases, the interrogator 108 may determine some or all of the calculations needed for determining an amount of force applied to patient's anatomy by the surgical device 102. Alternatively or additionally, the interrogator 108 may output some or all sensed data to a controller for calculating or determining a pressure applied to a patient's anatomy by the surgical device 102.

In some cases, before, while, or after determining forces applied to a patient's anatomy by a surgical device, an electrical stimulation may be applied to a patient's anatomy. In one example, the surgical device 102 may include a retractor incorporating the optical fiber-based sensor system 106 and an electrode nerve identification system and forces may be measured in conjunction with nerve identification to help mitigate damage to nerve tissue or other tissue. Once a nerve has been identified, the interrogator 108 or the controller may be configured to provide an estimate of an amount of force that is being applied to the detected nerve. Estimating the amount of force that is being applied to the detected nerve may take into account one or more of a direction of the nerve relative to the surgical device 102, a distance of the nerve relative to the surgical device 102, a calculated force or pressure being applied to the patient's anatomy by the surgical device 102, or other suitable factors.

In response to detecting a nerve, an indication may be provided on a user interface that a nerve has been detected. In addition to providing or displaying the indication, an estimate of force that is being applied to the nerve may be provided. In some cases, the providing the estimate of force that is being applied to the nerve may be an indication that a nerve has been detected, but other additional or alternative graphical or alphanumeric indications may be provided. The combination of neuromonitoring and force sensing can permit the system (e.g., and thereby the user) the ability to determine which specific nerves were affected by retraction and an amount of force applied to such nerves. Further, specific parameters for safe retraction time or retraction force can be customized (e.g., from a lookup table or predetermined algorithm) based on a nerve's proximity, direction, or other features detected via neuromonitoring. For example, a particular force appropriate when a nerve is a certain distance away (e.g., detected via neuromonitoring) may be inappropriate (e.g., too great) when the nerve is detected at a shorter distance away. Likewise, the detected direction of the nerve can be a factor in determining safe retraction time or force. Alerts or other features can be customized based on such parameters.

Further, using the optical fiber-based sensor system 106 may include comparing an amount of force applied to a patient's tissue by the surgical device to one or more thresholds. In response to determining an amount of force applied to the patient's tissue has passed the threshold, a timer may be initiated (e.g., automatically initiated by the optical fiber-based sensing system 106 or otherwise initiated), which may or may not be displayed on a screen. Such initiation of a timer may allow a user to understand how long a determined amount of force has been applied to the patient's tissue (e.g., nerve tissue or other tissue), as it may be determined a relatively small amount of force may be applied to tissue for a longer amount of time relative to an amount of time a larger amount of force could be applied to the tissue. In some cases, once the timer has been initiated, the timer (e.g., the elapsed time), an amount of force, and an indication that a nerve has been detected may be provided on a screen or otherwise may be provided on a user interface. As discussed above, the threshold can be set based on data obtained from neuromonitoring, such as a nerve's proximity to the retractor. In some examples, the timer may provide alerts upon passing a timer threshold (e.g., a predetermined number of minutes). The timer threshold may also be customized based on neuromonitoring, sensed force, or surgeon preference.

In addition to or as an alternative to determining an amount of force applied to a patient's tissue by the surgical device, the system may determine a position (e.g., a size or other suitable position) of an adjustable surgical device (e.g., retractor, a surgical dilator, an implant, a trial implant, and a surgical measurement tool etc.) based on the detected light. In one example, if an expected amount of force acting on the surgical device is known for different expansion amounts of an adjustable or expandable implant, the adjustable or expandable implant may be adjusted and an amount of adjustment or positioning (e.g., a height, width, length, or combination thereof) of the implant may be determined based on the determined force applied to the surgical devices or anatomy of the patient (e.g., in response to detecting reflected light with the fiber optic-sensor based system).

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The above detailed description should be read with reference to the drawings in which similar elements in different drawings are numbered the same. The drawings, which are not necessarily to scale, depict illustrative embodiments and are not intended to limit the scope of the invention.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A surgical system comprising:
   a surgical device configured for insertion to a surgical site, the surgical device comprising:
   a tissue contacting component having a first portion and a second portion, wherein the second portion is responsive to forces acting on the tissue contacting component; and
   an optical fiber including a sensing portion disposed along the second portion of the tissue contacting component, wherein the optical fiber is configured to deform in response to loads acting on the tissue contacting component;
   an interrogator coupled to the optical fiber, wherein the interrogator is configured to sense light reflected through the optical fiber and translate the sensed light into electrical signals; and wherein the electrical signals are indicative of loads acting on the tissue contacting component of the surgical device; and wherein the first portion of the tissue contacting component is constructed from a first material and the second portion of the tissue contacting component is constructed from a second material more responsive to loads acting on the tissue contacting component than the first material.

2. The surgical system of claim 1, wherein the surgical device comprises a removable body configured to be used in sensing nerve tissue adjacent the surgical device, wherein an electrode and the optical fiber are disposed in the removable body and the removable body is slidably coupled to the surgical device.

3. The surgical system of claim 1, wherein the interrogator includes a light emitter configured to emit a light through the optical fiber and a detector configured to sense the light reflected through the optical fiber.

4. A pressure sensing surgical device, comprising:
a component configured to be adjusted at or near a surgical site, the component has a tissue contacting surface;
an optical fiber extending adjacent to or through the component; and
a sensing portion of the optical fiber, the sensing portion of the optical fiber being configured to deform in response to loads acting on the tissue contacting surface caused by adjustment of the component; and
wherein the component includes a portion constructed from a first material and a portion constructed from a second material that is less rigid than the first material, the sensing portion of the optical fiber is disposed along the second material.

5. The pressure sensing surgical device of claim 4, further comprising:
wherein the sensing portion of the optical fiber includes up to twenty-five fiber Bragg gratings;
wherein the fiber Bragg gratings have a grating period of at least 1 millimeter (mm); and
wherein the fiber Bragg gratings include at least two fiber Bragg gratings having a grating period of 1 mm and at least two fiber Bragg gratings having a grating period of 10 mm.

6. The pressure sensing surgical device of claim 4, wherein the component is a retractor blade coupled to a retractor body.

7. The pressure sensing surgical device of claim 4, wherein the component is an expandable implant.

8. The pressure sensing surgical device of claim 4, wherein the component is an expandable trial.

9. The pressure sensing surgical device of claim 4, further comprising a plurality of optical fibers extending adjacent the component, the plurality of optical fibers including the optical fiber.

10. The pressure sensing surgical device of claim 4, wherein the component is a surgical drill bit.

11. A pressure sensing surgical device, comprising:
a component configured to be adjusted at or near a surgical site, the component has a tissue contacting surface;
an optical fiber extending adjacent to or through the component; and
a sensing portion of the optical fiber, the sensing portion of the optical fiber being configured to deform in response to loads acting on the tissue contacting surface caused by adjustment of the component; and
wherein the component is an expandable implant.

12. A pressure sensing surgical device, comprising:
a component configured to be adjusted at or near a surgical site, the component has a tissue contacting surface;
an optical fiber extending adjacent to or through the component; and
a sensing portion of the optical fiber, the sensing portion of the optical fiber being configured to deform in response to loads acting on the tissue contacting surface caused by adjustment of the component; and
wherein the component is an expandable trial.

13. A pressure sensing surgical device, comprising:
a component configured to be adjusted at or near a surgical site, the component has a tissue contacting surface;
an optical fiber extending adjacent to or through the component; and
a sensing portion of the optical fiber, the sensing portion of the optical fiber being configured to deform in response to loads acting on the tissue contacting surface caused by adjustment of the component; and
wherein the component is a surgical drill bit.

* * * * *